US012679814B2

(12) United States Patent
Andreae

(10) Patent No.: US 12,679,814 B2
(45) Date of Patent: Jul. 14, 2026

(54) SYNTHESIS OF PROSTATE SPECIFIC MEMBRANE ANTIGEN (PSMA) LIGANDS

(71) Applicant: NOVARTIS AG, Basel (CH)

(72) Inventor: Fritz Andreae, Raaba-Grambach (AT)

(73) Assignee: NOVARTIS AG, Basel (CH)

( * ) Notice: Subject to any disclaimer, the term of this patent is extended or adjusted under 35 U.S.C. 154(b) by 529 days.

(21) Appl. No.: 18/253,298

(22) PCT Filed: Nov. 19, 2021

(86) PCT No.: PCT/EP2021/082328

§ 371 (c)(1),
(2) Date: May 17, 2023

(87) PCT Pub. No.: WO2022/106633

PCT Pub. Date: May 27, 2022

(65) Prior Publication Data

US 2024/0010623 A1 Jan. 11, 2024

(30) Foreign Application Priority Data

Nov. 19, 2020 (EP) .................................... 20208561

(51) Int. Cl.
*C07D 257/02* (2006.01)

(52) U.S. Cl.
CPC .................................. *C07D 257/02* (2013.01)

(58) Field of Classification Search
CPC .................................................... C07D 257/02
See application file for complete search history.

(56) References Cited

FOREIGN PATENT DOCUMENTS

| | | | |
|---|---|---|---|
| CN | 109134602 | | 1/2019 |
| CN | 110305186 | A | 10/2019 |
| CN | 110305187 | A | 10/2019 |
| CN | 110317151 | A | 10/2019 |
| JP | 2019519467 | A | 7/2019 |
| WO | WO2005023314 | | 3/2005 |
| WO | WO2015055318 | | 4/2015 |
| WO | 2017165473 | A1 | 9/2017 |
| WO | WO2018223180 | | 12/2018 |
| WO | 2019157037 | A1 | 8/2019 |
| WO | 2020028323 | | 2/2020 |

OTHER PUBLICATIONS

Eder, Bioconjugate Chem, 2012, 2, 688-697. (Year: 2012).*
PCT Search Report and Written Opinion prepared for PCT Application No. PCT/EP2021/082328, completed Dec. 13, 2021.
Pratesi, Alessandro, et al., "Design and Solid Phase Synthesis of new DOTA Conjugated (+)-Biotin Dimers Planned to Develop Molecular Weight-Tuned Avidin Oligomers," 2015, Org. Biomol Chem., vol. 13, pp. 3988-4001.
Banerjee, Sangeeta Ray, et al., "Effect of Chelators on the Pharmacokinetics of 99mTc-Labeled Imaging Agents for the Prostate-Specific Membrane Antigen (PSMA)," 2013, J. Med Chem., vol. 56, No. 15, pp. 6108-6121.
Chan WC et al. "Fmoc-Solid Phase Peptide Synthesis-A practical approach passage", Mar. 1, 2000 (Mar. 1, 2000), FMOC Solid Phase Peptide Synthesis : A Practical Approach; [The Practical Approach Series , ISSN 0957-025X ; ZDB-10: 9132715 ; 222], Oxford University Press, GB, pp. X-XXIV.
Delker, Andreas, et al., "Dosimetry for 177Lu-DKFZ-PSMA-617: a New Radiopharmaceutical for the Treatment of Metastatic Prostate Cancer," 2016, European Journal of Nuclear Medicine and Molecular Imaging, vol. 43, No. 1, pp. 42-51.
Kiess, A. P., et al., "Prostate-Specific Membrane Antigen as a Target for Cancer Imaging and Therapy," 2015, Q J Nucl Med Mol Imaging., vol. 59, No. 3, pp. 241-268.
Benesova, Martina, et al., "Preclinical Evaluation of a Tailor-Made DOTA-Conjugated PSMA Inhibitor with Optimized Linker Moiety for Imaging and Endoradiotherapy of Prostate Cancer," 2015, J. Nucl. Med., No. 56, pp. 914-920.
Marchal, C., et al., Expression of Prostate Specific Membrane Antigen (PSMA) in Prostatic Adenocarcinoma and Prostatic Intraepithelial Neoplasia, 2004, Histol Histopathol, No. 19, pp. 715-718.
Benesova, Martina, et al., "Linker Modification Strategies to Control the Prostate-Specific Membrane Antigen {PSMA)-Targeting and Pharmacokinetic Properties of DOTA-Conjugated PSMA Inhibitors," 2016, J. Med. Chem., No. 59, pp. 1761-1775.
Eder, Matthias, et al., "68 Ga-Complex Lipophilicity and the Targeting Property of a Ure••Based PSMA Inhibitor for PET Imaging," 2012, BioConnjugate Chem., No. 23, pp. 688-697.
Mease, Ronnie C., et al., PET Imaging in Prostate Cancer: Focus on Prostate-Specific Membrane Antigen, 2013, Curr Top Med Chem., vol. 13, No. 8, pp. 951-962.

* cited by examiner

*Primary Examiner* — D Margaret M Seaman
(74) *Attorney, Agent, or Firm* — Barnes & Thornburg LLP

(57) ABSTRACT

The present disclosure relates to the synthesis of prostate specific membrane antigen (PSMA) ligands that are useful in the treatment of diseases like cancer. In particular, the disclosure relates to a method for synthesizing PSMA ligands having a glutamate-urea-lysine (GUL) moiety and a chelating agent that can comprise a radiometal.

16 Claims, 1 Drawing Sheet

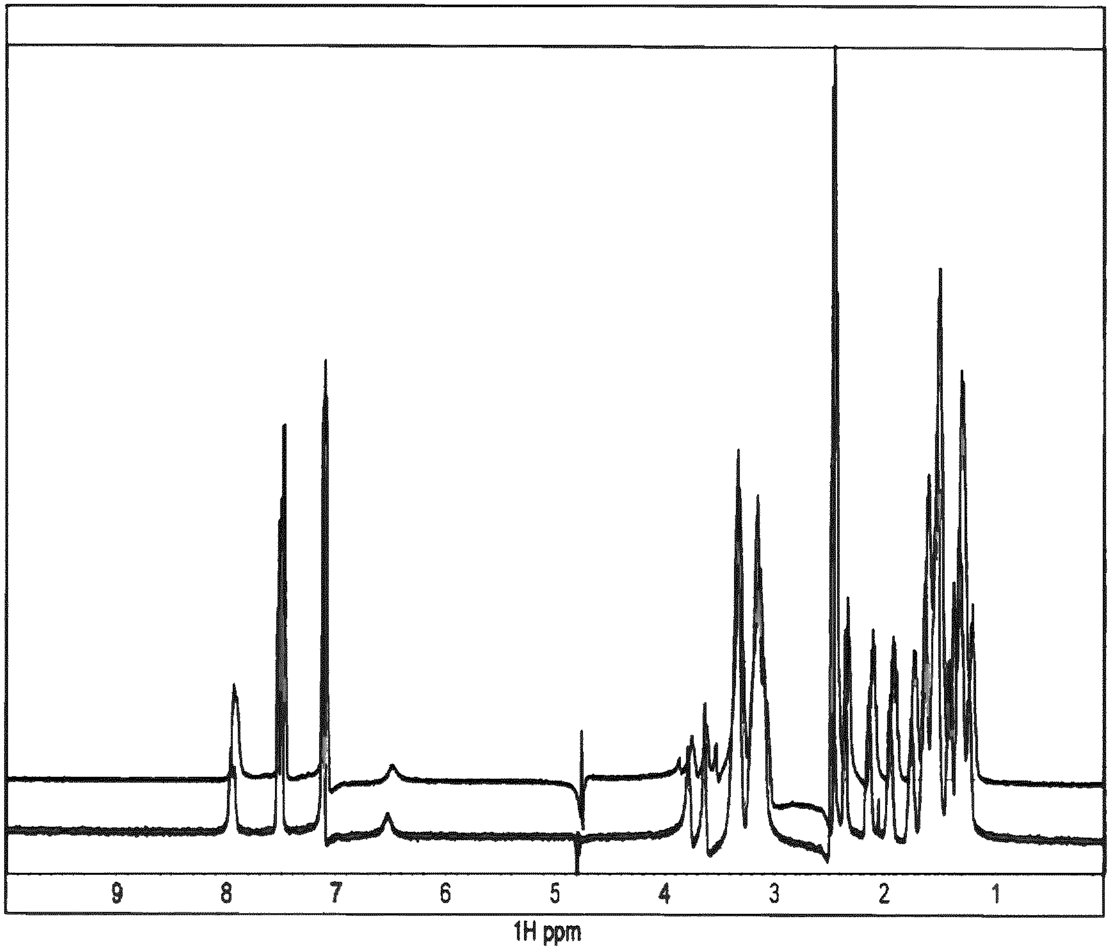
9
8
7
6
5
4
3
2
1
1H ppm

SYNTHESIS OF PROSTATE SPECIFIC MEMBRANE ANTIGEN (PSMA) LIGANDS

CROSS-REFERENCE TO RELATED APPLICATIONS

This application is a national stage entry of PCT International Application No. PCT/EP2021/082328, filed Nov. 19, 2021, which claims the benefit of European Patent Application No. 20208561.9, filed Nov. 19, 2020, the disclosure of each of which are each hereby incorporated by reference in their entirety.

TECHNICAL FIELD

The present disclosure relates to the synthesis of prostate specific membrane antigen (PSMA) ligands that are useful in the treatment of diseases like cancer. In particular, the disclosure relates to a method for synthesizing PSMA ligands having a glutamate-urea-lysine (GUL) moiety and a chelating agent that can comprise a radiometal.

BACKGROUND ART

Prostate cancer is one of the most widespread cancers in the US and in Europe. In particular, metastatic prostate cancer (mCRPC) is associated with poor prognosis and diminished quality of life.

Recently, a new development stream for treating prostate cancer is represented by the endo-radiotherapy based on PSMA ligands, as PSMA is considered to be a suitable target for imaging and therapy due to its over-expression in primary cancer lesions and in soft-tissue/bone metastatic disease. Also, PSMA expression seems to be even higher in the most aggressive castration-resistant variants of the disease, which represents a patient population with high unmet medical need. (Marchal et al., Histol Histopathol, 2004, July; 19(3):715-8; Mease et al., Curr Top Med Chem, 2013, 13(8):951-62).

Among many small-molecule ligands targeting PSMA, the urea-based low molecular weight agents have been the most extensively investigated ones. These agents were shown to be suitable for prostate cancer clinical assessment as well as for PRRT therapy (Kiess et al., Q J Nucl Med Mol Imaging, 2015; 59:241-68). Some of these agents have glutamate-urea-lysine (GUL) as the targeting scaffold. A class of molecules was created following the strategy to attach a linker between the chelator and GUL moiety. This approach allows the urea to reach the binding site while keeping the metal chelated portion on the exterior of the binding site. This strategy was successful in xenograft PSMA positive tumors due to its demonstrated high uptake and retention as well as fast renal clearance (Banerjee et al., J Med Chem, 2013; 56:6108-21).

WO2017/165473 also describes urea-based PSMA ligands labeled with $^{177}Lu$, which show radiotherapeutic efficacy in tumor-bearing mice.

Because of the interest in urea-based PSMA ligands, there is a need to provide synthesis methods that are cost-effective and that can deliver important quantities of product with a high purity.

SUMMARY OF THE DISCLOSURE

The present disclosure relates to a method for synthesizing a PSMA ligand that is useful in the treatment of diseases like cancer, and in particular prostate cancer.

The present disclosure also relates to a method for synthesizing a compound of formula (I), or a pharmaceutically acceptable salt thereof, using solid phase synthesis:

(I)

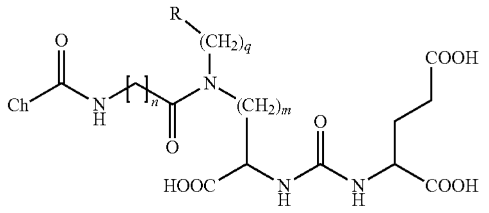

wherein

- m is an integer selected from the group consisting of 1, 2, 3, 4, and 5, preferably m is 4;
- q is an integer selected from the group consisting of 1, 2, 3, 4, 5, and 6, preferably q is 1;
- n is an integer selected from the group consisting of 1, 2, 3, 4, 5, and 6, preferably n is 4 or 5;
- R is selected from the group consisting of $C_6$-$C_{10}$ aryl and heteroaryl containing 5 to 10 ring atoms, said aryl and heteroaryl being substituted 1 or more times with X;
- X is —V—Y;
- V is a bond or a $C_1$-$C_6$ alkylene, preferably V is a bond;
- Y is a halogen; and
- Ch is a chelating agent, typically DOTA.

According to a first embodiment, the method comprises at least one of the following steps:

a) contacting a supported, preferably a resin-based, compound of formula (II)

(II)

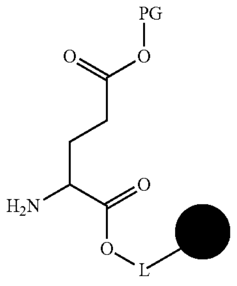

with a compound of formula (III)

(III)

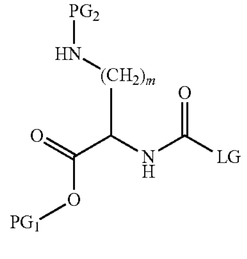

to provide a supported, preferably a resin-based, compound of formula (IV)

(IV)

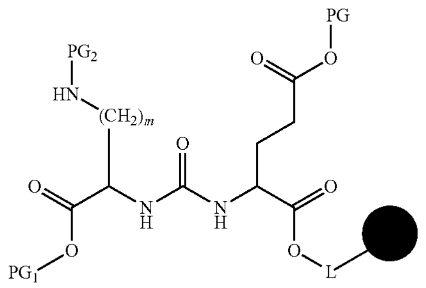

b) contacting the supported, preferably the resin-based, compound of formula (IV) with a deprotecting agent to provide a supported, preferably a resin-based, compound of formula (V)

(V)

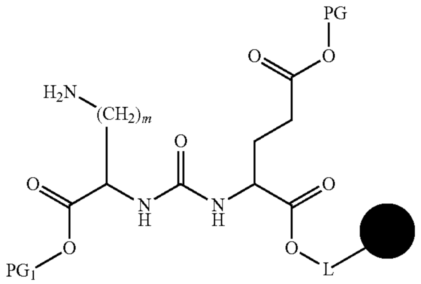

c) contacting the supported, preferably the resin-based, compound of formula (V) with a compound of formula (VI)

(VI)

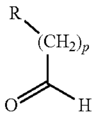

to provide a supported, preferably a resin based, compound of formula (VIII (VII)

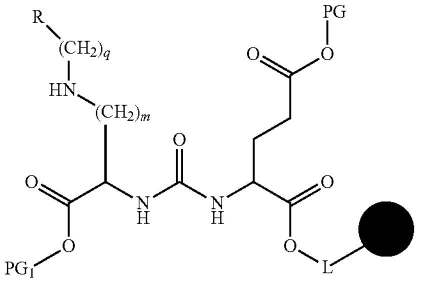

d) contacting the supported, preferably the resin-based, compound of formula (VII) with a compound of formula (VIII)

(VIII)

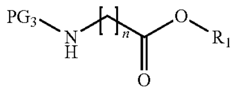

to provide a supported, preferably a resin-based, compound of formula (IX)

(IX)

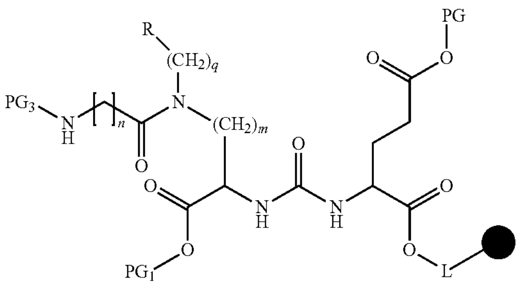

e) contacting the supported, preferably the resin-based, compound of formula (IX) with a deprotecting agent to provide a supported, preferably a resin-based, compound of formula (X)

(X)

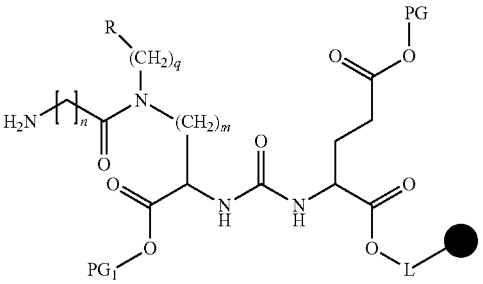

f) contacting the supported, preferably the resin-based, compound of formula (X) with a compound of formula (XI)

(XI)

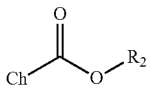

to provide a supported, preferably a resin-based, compound of formula (XII)

(XII)

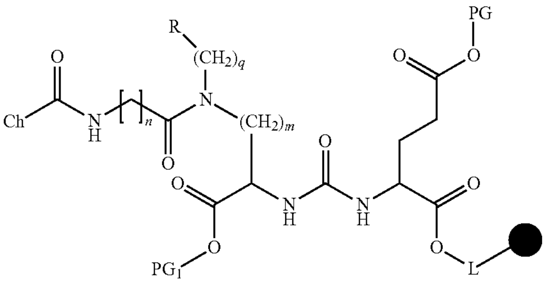

g) contacting the supported, preferably the resin-based, compound of formula (XII) with a cleavage reagent, and optionally with a deprotecting agent, to provide the compound of formula (I)

wherein

PG, and PG1 are each independently a carboxyl protecting group a carboxyl protecting group;

L is a linker;

PG2 and PG3 are each independently an amino protecting group;

R1 and R2 are each independently H, an activating ester group;

LG is a leaving group selected from the group consisting of imidazole, halogens and activating ester groups;

m is an integer selected from the group consisting of 1, 2, 3, 4, and 5, preferably m is 4;

q is an integer selected from the group consisting of 1, 2, 3, 4, 5, and 6, preferably q is 1;

p=q−1

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene, preferably V is a bond; and

Y is a halogen;

n is an integer selected from the group consisting of 1, 2, 3, 4, 5, and 6, preferably n is 4 or 5; and Ch is a chelating agent, typically DOTA.

According to a second embodiment, the method comprises at least one of the following steps:

a') contacting a supported, preferably a resin-based, compound of formula (II')

(II')

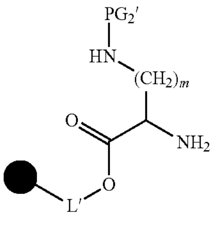

with a compound of formula (III')

(III')

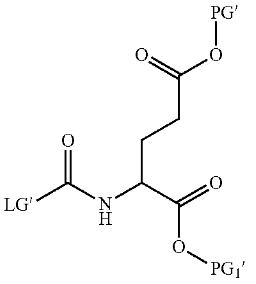

to provide a supported, preferably a resin-based, compound of formula (IV')

(IV')

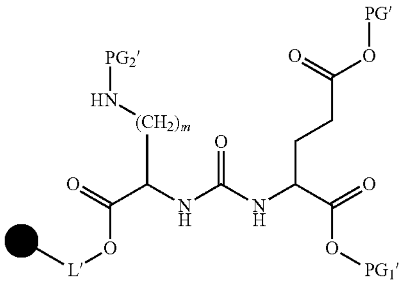

b') contacting the supported, preferably the resin-based, compound of formula (IV') with a deprotecting agent to provide a supported, preferably a resin-based, compound of formula (V')

(V')

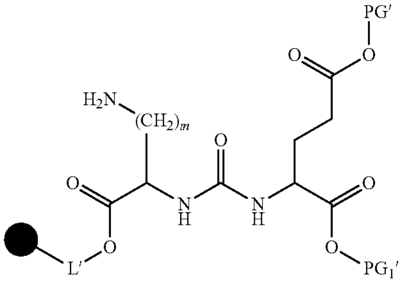

c') contacting the supported, preferably the resin-based compound of formula (V') with a compound of formula (VI')

(VI')

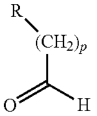

to provide a supported, preferably a resin based, compound of formula (VII')

(VII')

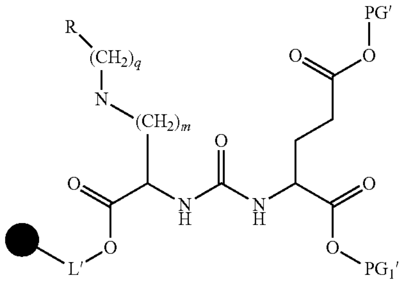

d') contacting the supported, preferably the resin-based, compound of formula (VII') with a compound of formula (VIII')

(VIII')

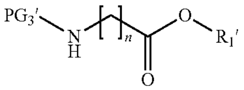

to provide a supported, preferably a resin-based, compound of formula (IX')

(IX')

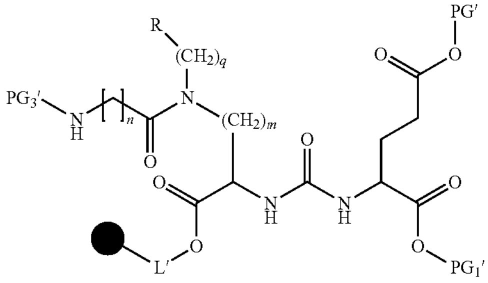

e') contacting the supported, preferably the resin-based, compound of formula (IX') with a deprotecting agent to provide a supported, preferably a resin-based compound of formula (X')

(X')

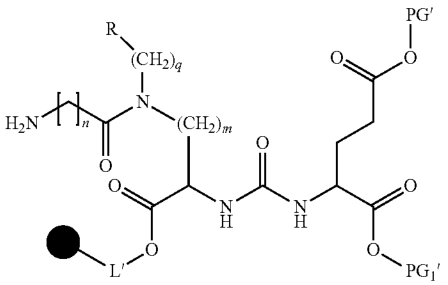

f') contacting the supported, preferably the resin-based, compound of formula (X') with a compound of formula (XI')

(XI')

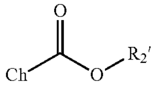

to provide a supported, preferably a resin-based, compound of formula (XII')

(XII')

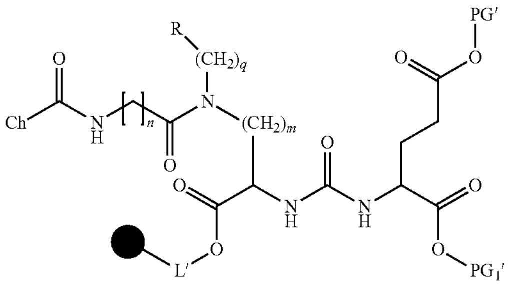

g') contacting the supported, preferably the resin-based compound of formula (XII') with a cleavage reagent, and optionally with a deprotecting agent, to provide the compound of formula (I), Wherein PG', and PG1' are each independently a carboxyl protecting group a carboxyl protecting group;

L' is a linker;

PG2' and PG3' are each independently an amino protecting group;

R1' and R2' are each independently H, an activating ester group;

LG' is a leaving group selected from the group consisting of imidazole, halogens and activating ester groups;

m is an integer selected from the group consisting of 1, 2, 3, 4, and 5, preferably m is 4;

q is an integer selected from the group consisting of 1, 2, 3, 4, 5, and 6, preferably q is 1;

p=q−1

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene, preferably V is a bond; and

Y is a halogen;

n is an integer selected from the group consisting of 1, 2, 3, 4, 5, and 6, preferably n is 4 or 5; and Ch is a chelating agent, typically DOTA.

The fact that the synthesis is performed using solid phase synthesis allows for an efficient synthesis which is cost-effective. In particular, the overall yield of the synthesis can be greater than or equal to 10%, based on the supported starting material, compound (II) or (II').

DETAILED DESCRIPTION

Definitions

As used herein, the terms "solid phase synthesis" refer to a synthesis of chemical compounds whereby the reactant molecule is chemically bound to an insoluble material (a solid support, typically a resin) and reagents are added in the solution-phase. The reactant molecule is usually chemically bound to the solid support through a linker. Solid phase synthesis is commonly used to synthesize peptide, the person skilled in the art is therefore familiar with the techniques and apparatus used to perform solid phase synthesis. In solid phase peptide synthesis, an amino acid or peptide is bound, usually via the C-terminus, to a solid support. New amino acids are added to the bound amino acid or peptide via coupling reactions. Due to the possibility of unintended reactions, protection groups are typically used. The use of solid phase synthesis makes it possible to isolate and purify intermediates by simple filtration and rinsing, avoiding long and costly isolation and purification of intermediates.

As used herein, the terms "supported compound" refer to a compound which is chemically bound to an insoluble material, typically a resin.

As used herein, the terms "resin-based compound" refer to a compound that is chemically bound to a resin, which is a solid support. The resin-based compound is used in solid phase synthesis.

As used herein, the term "linker" refers to a divalent moiety connecting the reactant molecule to the insoluble material.

As used herein, the terms "protecting group" refers to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007).

Protecting groups for protection of the carboxyl group, as described by Wutz et al. (pages 533-643), are used in certain embodiments. In some embodiments, the protecting group is removable by treatment with acid. Representative examples of carboxyl protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required.

Protecting group for protection of the amino group as described by Wutz et al. (pages 696-927), are used in certain embodiments. Representative examples of amino protecting groups include, but are not limited to, t-butyloxycarbonyl (Boc), 9-fluorenyl methoxycarbonyl (Fmoc), allyloxycarbonyl (alloc), N-(1-(4,4-dimethyl-2,6-dioxocyclohexylidene) ethyl) (Dde), 1-(1-Adamantyl)-1-Methylethoxycarbonyl (Adpoc), N-(1-(4,4-dimethyl-2,6-dioxocyclohex-1-ylidene)-3-methylbutyl) (ivDde), monomethoxytrityl (MMt) and 4-methyltrityl (Mtt). Persons skilled in the art will recognize appropriate situations in which protecting groups are required.

As used herein, the terms "activating ester group" refers to an electron-withdrawing group used to activate the ester function and make it more susceptible to nucleophilic attack. Active esters are commonly used in organic chemistry. Among activating ester groups, one can cite succinimidyl, p-nitrophenyl, tetrafluorophenyl, 3,4-dihydro-4-oxo-1,2,3-benzotriazine-3-yl, pentafluorophenyl, and 2,4,5-trichlorophenyl.

As used herein, the term "aryl" refers to a polyunsaturated, aromatic hydrocarbyl group having a single ring or multiple aromatic rings fused together, containing 6 to 10 ring atoms, wherein at least one ring is aromatic. The aromatic ring may optionally include one to two additional rings (cycloalkyl, heterocyclyl or heteroaryl as defined herein) fused thereto. Suitable aryl groups include phenyl, naphtyl and phenyl ring fused to a heterocyclyl, like benzopyranyl, benzodioxolyl, benzodioxanyl and the like.

As used herein, the term "alkyl", by itself or as part of another substituent, refers to a linear or branched alkyl functional group having 1 to 6 carbon atoms. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

As used herein, the term "halogen" refers to a fluoro (—F), chloro (—Cl), bromo (—Br), or iodo (—I) group.

As used herein, the term "heteroaryl" refers to a polyunsaturated, aromatic ring system having a single ring or multiple aromatic rings fused together or linked covalently, containing 5 to 10 atoms, wherein at least one ring is aromatic and at least one ring atom is a heteroatom selected from N, O and S. The nitrogen and sulfur heteroatoms may optionally be oxidized and the nitrogen heteroatoms may optionally be quaternized. Such rings may be fused to an aryl, cycloalkyl or heterocyclyl ring. Non-limiting examples of such heteroaryl, include: furanyl, thiophenyl, pyrrolyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzothiadiazolyl, quinolinyl, isoquinolinyl, cinnolinyl, quinazolinyl and quinoxalinyl.

Various embodiments of the disclosure are described herein. It will be recognized that features specified in each embodiment may be combined with other specified features to provide further embodiments.

The present disclosure encompasses the compounds of formula (I)-(XIV) and (I') to (XII'), their stereoisomers, tautomers, enantiomers, diastereomers, racemates or mixtures thereof, and their hydrates, solvates or pharmaceutically acceptable salts.

The terms "pharmaceutically acceptable salts" refers to salts that retain the biological effectiveness and properties of the compounds of this disclosure and, which typically are not biologically or otherwise undesirable. Examples of pharmaceutically acceptable salts include trifluoroacetic acid (TFA), acetate or hydrochloride salts.

Synthesis of the Compound of Formula (I)

The present disclosure also relates to a method for synthesizing a compound of formula (I), or a pharmaceutically acceptable salt, using solid phase synthesis:

(I)

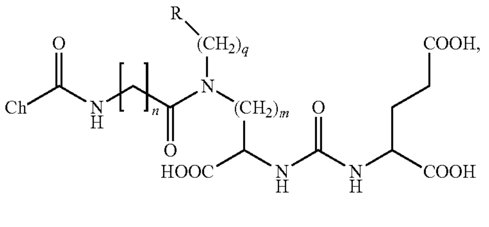

wherein m is an integer selected from the group consisting of 1, 2, 3, 4, and 5, preferably m is 4;

q is an integer selected from the group consisting of 1, 2, 3, 4, 5, and 6, preferably q is 1;

n is an integer selected from the group consisting of 1, 2, 3, 4, 5, and 6, preferably n is 4 or 5;

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene, preferably V is a bond;

Y is a halogen; and

Ch is a chelating agent, typically DOTA;

According to an embodiment, R is selected from the group consisting of $C_6$-$C_{10}$ aryl substituted with one or more halogen and pyridine substituted with one or more halogen.

According to an embodiment, R is selected from the group consisting of:

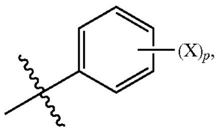

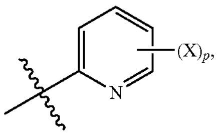

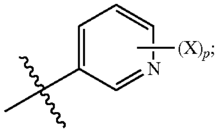

and

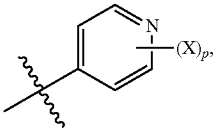

wherein p is an integer selected from the group consisting of 1, 2, 3, 4, and 5, preferably p is 1.

According to a specific embodiment, R is selected from

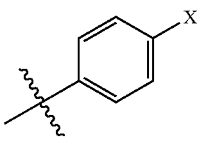

and

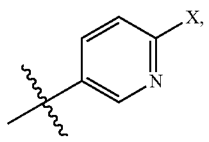

and, more preferably R is

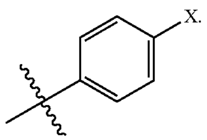

According to a specific embodiment, X is selected from Br and I.

Advantageously, R is

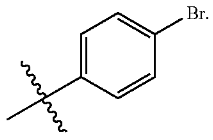 [SMILES: *c1ccc(Br)cc1]

Ch can be selected from the group consisting of:

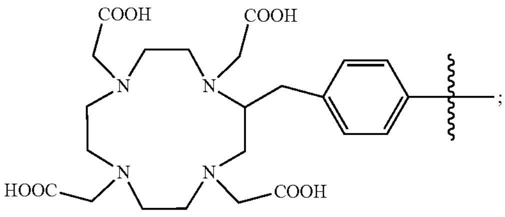

;

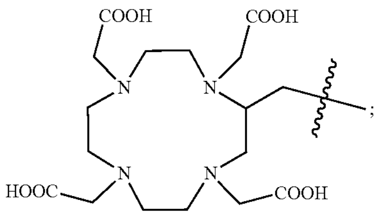

;

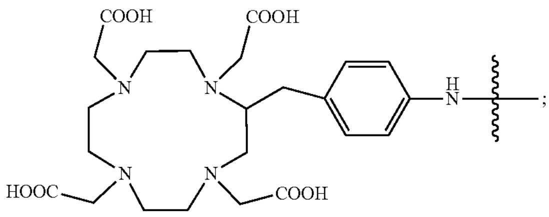

;

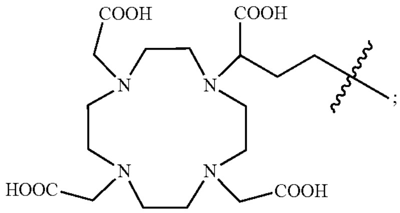

;

-continued

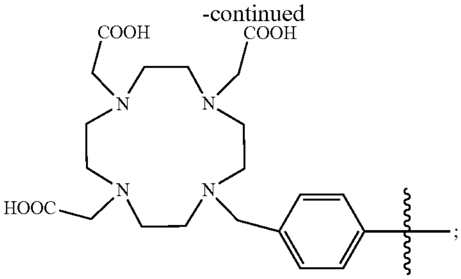

; and

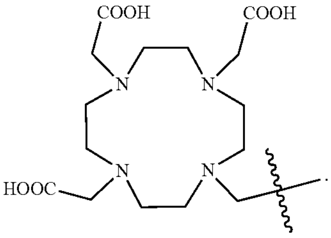

According to a specific embodiment, Ch is

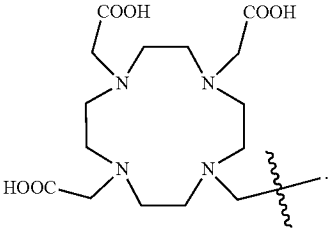 [SMILES: *CN1CCN(CC(=O)O)CCN(CC(=O)O)CCN(CC(=O)O)CC1]

During the synthesis of the compound of formula (I), Ch can be protected. In particular, the carboxylic acids of Ch can be protected with a protecting group which can be the same as PG, PG1, PG' or PG1'.

In specific embodiments, according to an embodiment, R is

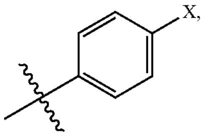

and Ch is

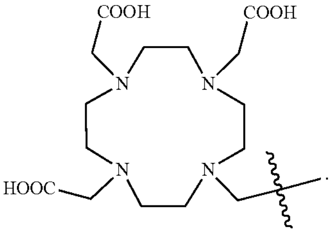 [SMILES: *CN1CCN(CC(=O)O)CCN(CC(=O)O)CCN(CC(=O)O)CC1]

According to a preferred embodiment, the compound of formula (I) is a compound of formula (XIII):

(XIII)

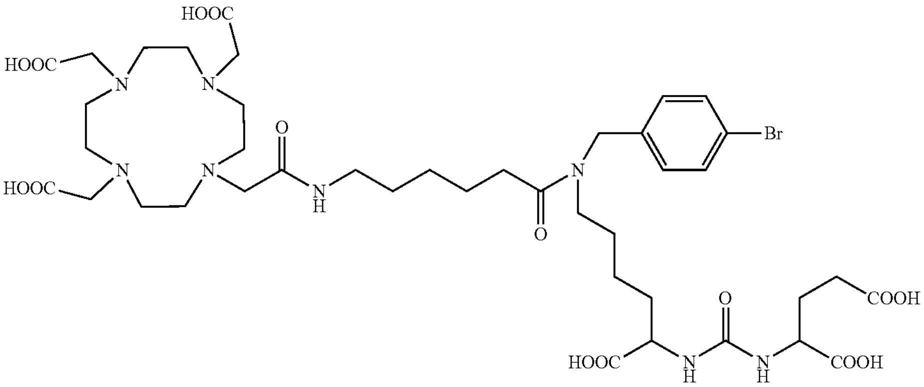

The compound of formula (XIII) can be referred to as PSMA-R2.

According to another embodiment, the compound of formula (I) is a compound of formula (XIV):

(XIV)

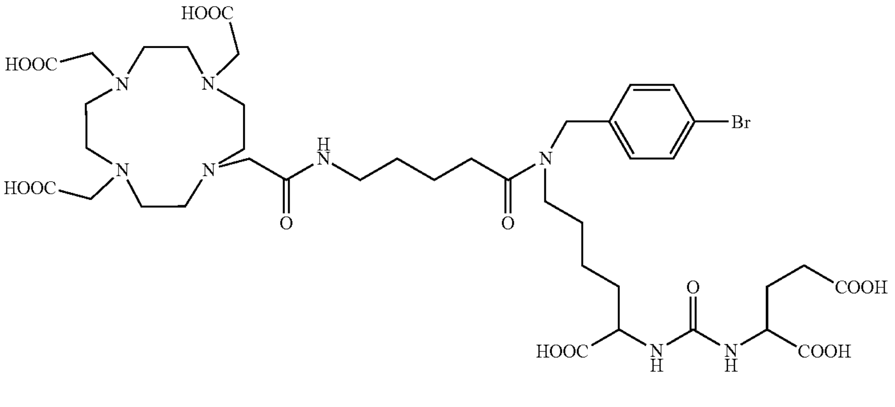

The compound of formula (XIV) can be referred to as PSMA-Cpd 2

According to an embodiment, the compound of formula (I) is a trifluoroacetic acid (TFA) salt, or an acetate salt.

The resin used in the present process can be any type of resin conventionally used in solid phase synthesis. These resins are well known to the person skilled in the art. Among resins, one can cite polystyrene resin, like microporous polystyrene resin or macroporous polystyrene resin, polyacrylamide resins, and copolymers resins. The linker L or L' is preferably an acid labile linker. The acid labile linker can be cleaved during step f) or f) when acid conditions are used. The linker L or L' varies depending on the resin used, and are well known to the person skilled in the art. Among resins comprising a linker group L or L', one can cite p-alkoxybenzyl alcohol resin (Wang resin), 4-(1',1'-dimethyl-1'-hydroxypropyl)phenoxyacetyl-alanyl-aminomethyl resin (DHPP resin), diphenyldiazomethane resin, (PDDM resin), trityl-chloride and 2-chlorotrityl chloride resin.

Each of the protecting groups PG, PG1, PG' and PG1' can be independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr) According to an embodiment, PG, and PG1 are tertiary butyl (t-Bu). According to an embodiment, PG', and PG1' are tertiary butyl (t-Bu)

Each of the protecting groups PG2, PG3, PG2' and PG3' can be independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably from the group consisting of Dde, ivDde and Fmoc.

According to an embodiment PG2 and PG3 is 9-fluorenyl methoxycarbonyl (Fmoc). According to an embodiment PG2' is N-(1-(4,4-dimethyl-2,6-dioxocyclohex-1-ylidene)-3-methylbutyl) (ivDde) or Dde, and PG3' is 9-fluorenyl methoxycarbonyl (Fmoc).

Dde and ivDde are the preferred protecting groups for PG2'. In particular, the deprotection of these groups does not require the use of a metal catalyst, on the contrary to the Alloc protecting group, which is removed using $Pd(PPh_3)_4$. Moreover, these groups are less bulky than MMt and Mtt, so that the loading on the resin can be higher, and they are less sensitive to acidic conditions than Mtt Each of the groups R1, R2, R1' and R2' can be independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably from the group consisting of H and succinimidyl. According to an embodiment, R1 and R2 are H. According to an embodiment, R1' and R2' are H.

LG and LG' are leaving groups that are independently selected from imidazole, halogens and activating ester groups. Among halogen, one can cite chloride. The fact that compounds (III) and (III') have a —NH—(CO)-LG or LG' moiety, and not a —N═C═O reactive moiety, makes it possible to synthesize the compound of formula (I) without the use of toxic compounds like phosgene or triphosgene, which are very hazardous products. LG or LG' is preferably an imidazole, as it can be synthesized without using of phosgene or triphosgene, which are very hazardous products. Moreover, when imidazole is used as a leaving group, the product is a stable solid, which can be easily handled.

According to a preferred embodiment, the method for synthesizing the compound of formula (I) comprises all the steps a)-g), or all of the steps a')-g').

Each of steps a)-g) or a')-g') can be performed at room temperature or under heating, for example at a temperature between 25 and 70° C. Each of steps a)-g) or a')-g') can be performed for a period of time between 5 minutes and 3 hours. Each of steps a)-g) or a')-g') can be performed under inert atmosphere, for example under argon.

In between each step, the resulting supported compound can be washed with a solvent, like dimethylformamide (DMF) or dichloromethane (DCM), isopropanol (IPA). It can also be alternately washed with different solvents, like alternating DMF and IPA washing.

Each of steps a)-g) or a')-g') can be performed using a polar aprotic solvent. According to an embodiment, the polar aprotic solvent that can be used in each of steps a) to g) or a')-g') is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO). Advantageously, the polar aprotic solvent that can be used in any of steps a) to g) or a' to g') is dimethylformamide (DMF).

Each of step a), d), f), a'), d') and f) can be performed using a coupling agent and/or a base. The base that can be used in each of step a), d), f), a'), d') and f) can be selected from the group consisting of N,N-Diisopropylethylamine ($^{i}$Pr2NEt), triethylamine (TEA), 4-methylmorpholine (NMM), imidazole, pyridine, and collidine, preferably the base is DIPEA. The coupling agent that can be used in any of step a), d), f), a'), d' and f) can be independently selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxide hexafluorophosphate (HATU), 2-(1H-Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethylamino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methylmorpholinium chloride (DMTMM), preferably from the group consisting of PyBOP and TBTU.

According to an embodiment, step a) is performed using a base, typically DIPEA. According to an embodiment, step a') is performed using a base, typically DIPEA. According to an embodiment, step d) is performed using a coupling agent and a base, typically TBTU and DIPEA. According to an embodiment, step d') is performed using a coupling agent and a base, typically TBTU and DIPEA. According to an embodiment, step f) is performed using a coupling agent and a base, typically PyBOP and DIPEA. According to an embodiment, step f) is performed using a coupling agent and a base, typically PyBOP and DIPEA.).

The deprotecting agent used in any of step b), e), b') and e') can be selected from the group consisting of hydrazine, piperidine, morpholine, 1,8-Diazabicyclo[5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine. According to an embodiment, the deprotecting agent used in step b) is piperidine. According to an embodiment, the deprotecting agent used in step b') is hydrazine. According to an embodiment, the deprotecting agent used in step e) is piperidine. According to an embodiment, the deprotecting agent used in step e') is piperidine.

Preferably, step c) is performed using a reductive agent, like $NaBH_4$ or $NaBH_3CN$.

The cleavage reagent of step g) or g') can be trifluoroacetic acid (TFA) or a trifluoroacetic acid (TFA)/water/triisopropylsilane mixture.

According to an embodiment, the overall yield of the synthesis can be greater than or equal to 10%, based on the supported starting material, compound (II) or (II'), preferably greater than or equal to 12%. The overall yield can be between 10 and 100%.

In some cases, the present method can also comprise a deprotection step to give compound (II), prior to step a).

In some cases, the present method can also comprise a deprotection step to give compound (II'), prior to step a').

EMBODIMENTS

The following specific embodiments are disclosed:

1. A method for synthesizing a compound of formula (I), or a pharmaceutically acceptable salt thereof, using solid phase synthesis:

(I)

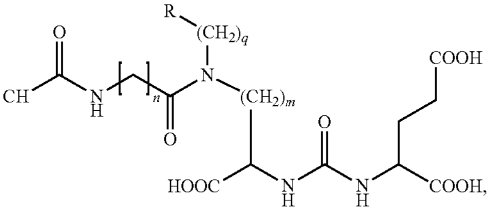

wherein m is an integer selected from the group consisting of 1, 2, 3, 4, and 5, preferably m is 4;

q is an integer selected from the group consisting of 1, 2, 3, 4, 5, and 6, preferably q is 1;

n is an integer selected from the group consisting of 1, 2, 3, 4, 5, and 6, preferably n is 4 or 5;

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene, preferably V is a bond;

Y is a halogen; and

Ch is a chelating agent, typically DOTA;

2. The method according to embodiment 1, wherein R is selected from

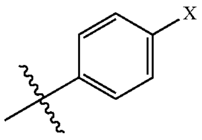

and

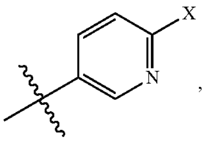

, and, preferably R is

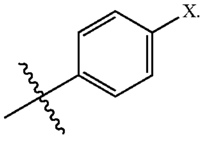

3. The method according to any of embodiments 1-2, wherein Ch is selected from the group consisting of:

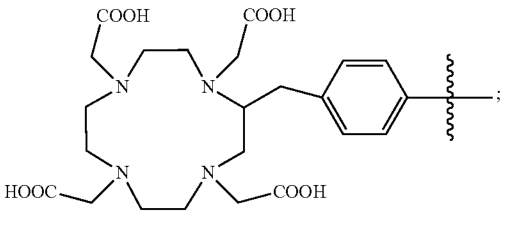

-continued
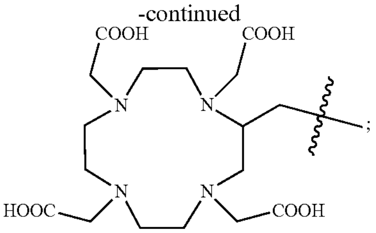
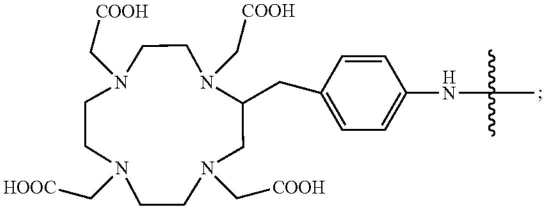
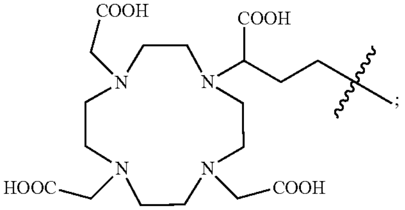
-continued
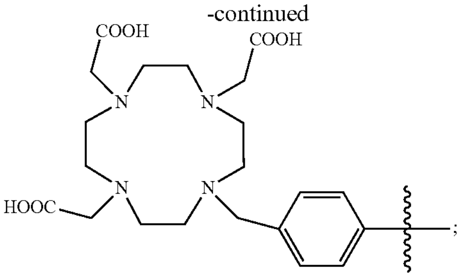
and
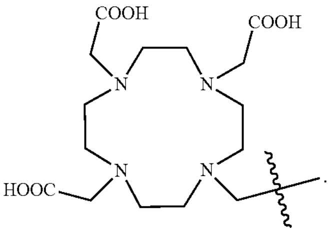
4. The method according to any of embodiments 1-3, wherein said compound of formula (I) is a compound of formula (XIII)
(XIII)
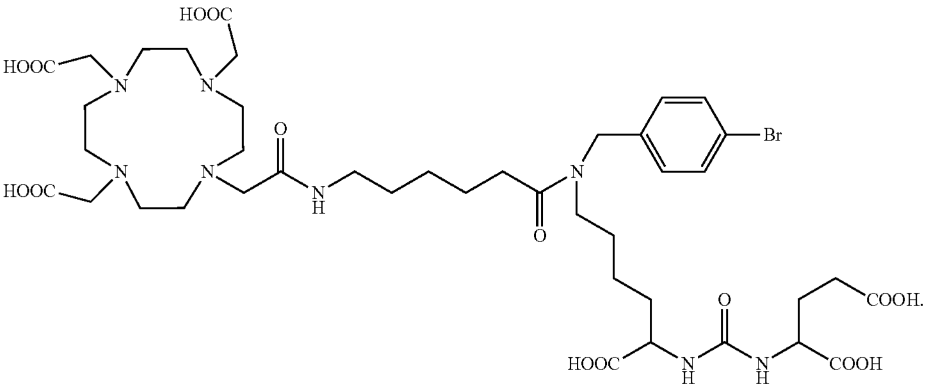
5. The method according to any of embodiments 1-3, wherein said compound of formula (I) is a compound of formula (XIV)
(XIV)
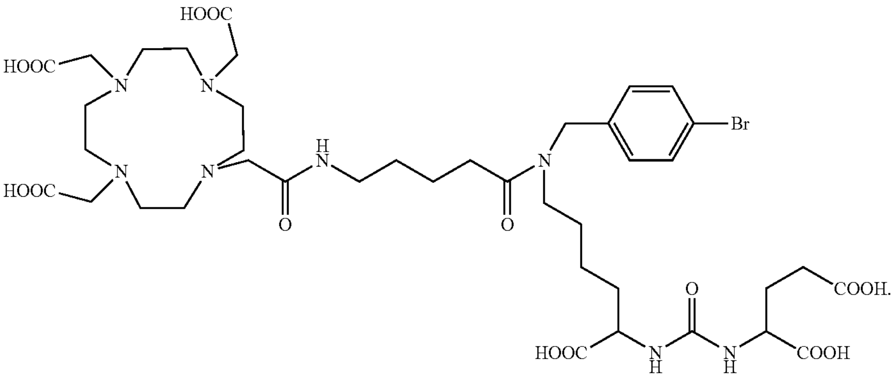

6. The method according to any of embodiments 1-5, wherein said method comprises at least one of the following step:

a) contacting a supported, preferably a resin-based, compound of formula (II)

(II)

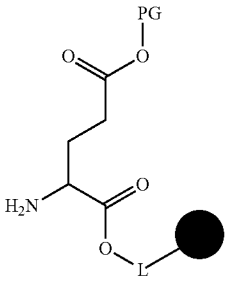

with a compound of formula (III)

(III)

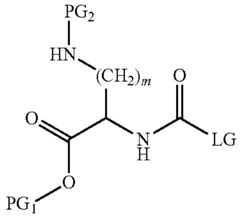

to provide a supported, preferably a resin-based, compound of formula (IV)

(IV)

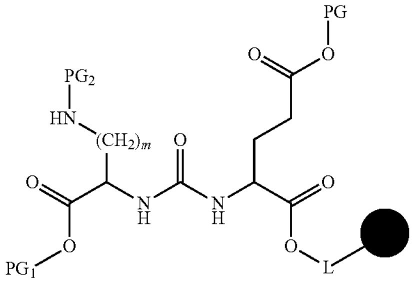

b) contacting the supported, preferably the resin-based, compound of formula (IV) with a deprotecting agent to provide a supported, preferably a resin-based, compound of formula (V)

(V)

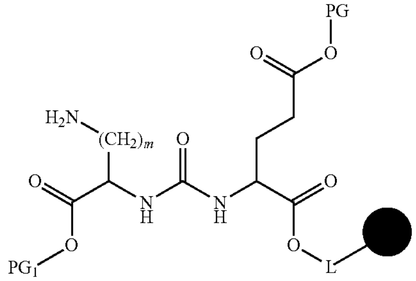

c) contacting the supported, preferably the resin-based, compound of formula (V) with a compound of formula (VI)

(VI)

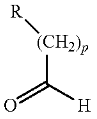

to provide a supported, preferably a resin based, compound of formula (VII)

(VII)

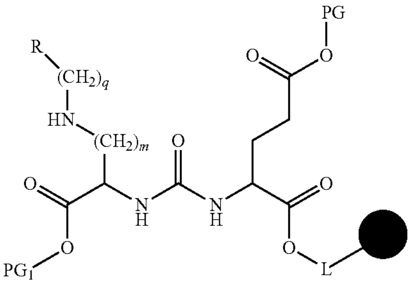

d) contacting the supported, preferably the resin-based, compound of formula (VII) with a compound of formula (VIII)

(VIII)

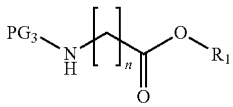

to provide a supported, preferably a resin-based, compound of formula (IX)

(IX)

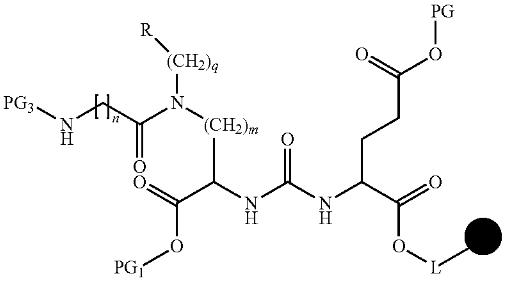

e) contacting the supported, preferably the resin-based, compound of formula (IX) with a deprotecting agent to provide a supported, preferably a resin-based, compound of formula (X)

(X)

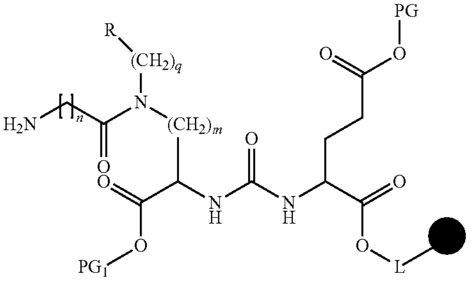

f) contacting the supported, preferably the resin-based, compound of formula (X) with a compound of formula (XI)

(XI)

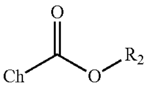

to provide a supported, preferably a resin-based, compound of formula (XII)

(XII)

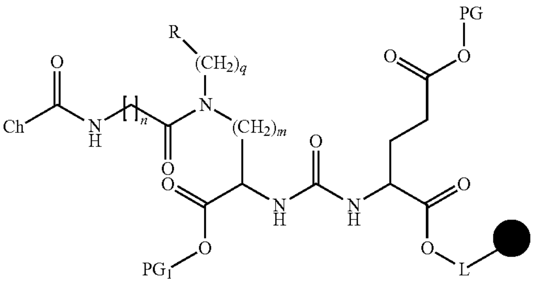

g) contacting the supported, preferably the resin-based, compound of formula (XII) with a cleavage reagent, and optionally with a deprotecting agent, to provide the compound of formula (I)

wherein

PG, and PG1 are each independently a carboxyl protecting group a carboxyl protecting group;

L is a linker;

PG2 and PG3 are each independently an amino protecting group;

R1 and R2 are each independently H, an activating ester group;

LG is a leaving group selected from the group consisting of imidazole, halogens and activating ester groups p=q−1.

7. The method according to embodiment 6, wherein said method comprises all the steps a) to g).
8. The method according to any of embodiments 6-7, wherein PG, and PG1 are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr), preferably PG, and PG1 are tertiary butyl (t-Bu).
9. The method according to any of embodiments 6-8, wherein PG2, and PG3, are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably, PG2 and PG3 are 9-fluorenyl methoxycarbonyl (Fmoc).
10. The method according to any of embodiments 6-9, wherein R1 and R2 are independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably R1 and R2 are independently selected from the group consisting of H or succinimidyl.
11. The method according to any of embodiments 6-10 wherein at least one of the steps a)-g) is performed using a polar aprotic solvent.
12. The method according to embodiment 11, wherein the polar aprotic solvent is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO), preferably, the solvent is dimethylformamide (DMF).
13. The method according to any of embodiments 6-12, wherein at least one of the step a), d) or f) is performed using a coupling agent and/or a base.
14. The method according to embodiment 13, wherein the base is selected from the group consisting of N,N-Diisopropylethylamine (DIPEA), N,N-Diisopropylethylamine ($^i$Pr2NEt), triethylamine (TEA), 4-methylmorpholine (NMM), imidazole, pyridine, and collidine.
15. The method according to embodiment 13 or 14, wherein the coupling agent is selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxide hexafluorophosphate (HATU), 2-(1H-

Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethylamino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methyl-morpholinium chloride (DMTMM).

16. The method according to any of embodiments 13-15, wherein step a) is performed using a base, typically DIPEA, step d) is performed using a coupling agent and a base, typically TBTU and DIPEA, and step f) is performed using a coupling agent and a base, typically PyBOP and DIPEA.

17. The method according to any of embodiments 6-16, wherein the deprotecting agent that is used in step b) and/or e) is selected from the group consisting of hydrazine, piperidine, morpholine, 1,8-Diazabicyclo[5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine.

18. The method according to any of embodiments 6-17, wherein step c) is performed using a reductive agent, preferably selected from $NaBH_4$ and $NaBH_3CN$.

19. The method according to any of embodiments 6-18, wherein step g) is performed using trifluoroacetic acid (TFA) or a trifluoroacetic acid (TFA)/water/triisopropylsilane mixture.

20. The method according to any of embodiments 1-5, wherein said method comprises at least one of the following steps:

a') contacting a supported, preferably a resin-based, compound of formula (II')

(II')

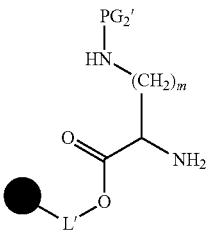

with a compound of formula (III')

(III')

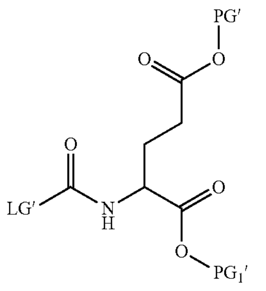

to provide a supported, preferably a resin-based, compound of formula (IV')

(IV')

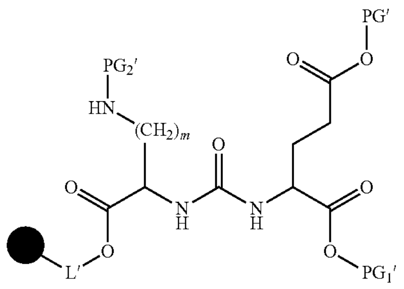

b') contacting the supported, preferably the resin-based, compound of formula (IV') with a deprotecting agent to provide a supported, preferably a resin-based, compound of formula (V')

(V')

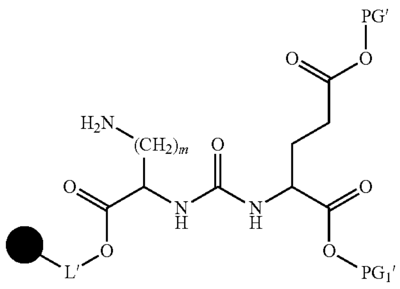

c') contacting the supported, preferably the resin-based compound of formula (V') with a compound of formula (VI')

(VI')

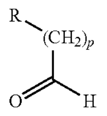

to provide a supported, preferably a resin based, compound of formula (VII')

(VII')

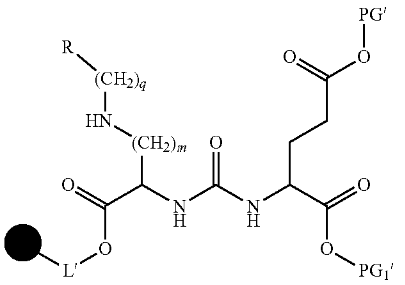

d') contacting the supported, preferably the resin-based, compound of formula (VII') with a compound of formula (VIII')

(VIII')

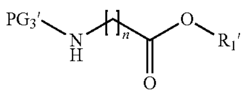

to provide a supported, preferably a resin-based, compound of formula (IX')

(IX')

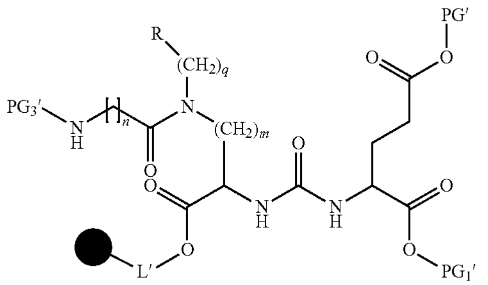

e') contacting the supported, preferably the resin-based, compound of formula (IX') with a deprotecting agent to provide a resin-based compound of formula (X')

(X')

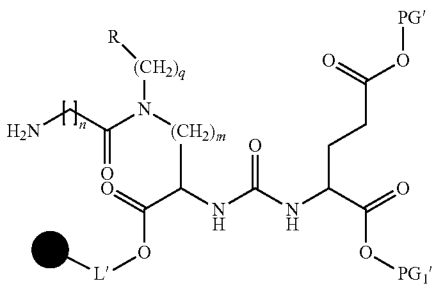

f) contacting the supported, preferably the resin-based, compound of formula (X') with a compound of formula (XI')

(XI')

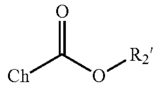

to provide a supported, preferably a resin-based, compound of formula (XII')

(XII')

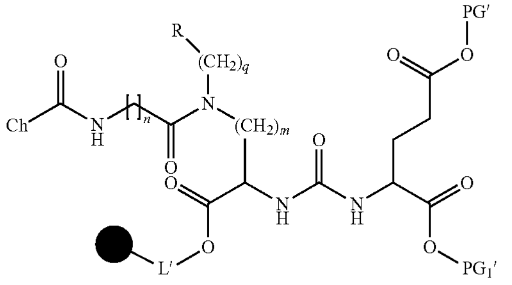

g') contacting the supported, preferably the resin-based compound of formula (XII') with a cleavage reagent, and optionally with a deprotecting agent, to provide the compound of formula (I), Wherein PG', and PG1' are each independently a carboxyl protecting group a carboxyl protecting group;

L' is a linker;

PG2' and PG3' are each independently an amino protecting group;

R1' and R2' are each independently H, an activating ester group;

LG' is a leaving group selected from the group consisting of imidazole, halogens and activating ester groups;

p=q−1.

21. The method according to embodiment 20, wherein said method comprises all the steps a') to g').
22. The method according to any of embodiments 20-21, wherein PG', and PG1' are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr), preferably PG', and PG1' are tertiary butyl (t-Bu).
23. The method according to any of embodiments 20-22, wherein PG2', and PG3', are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably, PG2' is Dde or ivDde, and PG3' is 9-fluorenyl methoxycarbonyl (Fmoc).
24. The method according to any of embodiments 20-23, wherein R1' and R2' are independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably R1' and R2' are independently selected from the group consisting of H or succinimidyl.

25. The method according to any of embodiments 20-24 wherein at least one of the steps a')-g') is performed using a polar aprotic solvent.
26. The method according to embodiment 25, wherein the polar aprotic solvent is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO), preferably, the solvent is dimethylformamide (DMF).
27. The method according to any of embodiments 20-26, wherein at least one of the step a'), d') or f) is performed using a coupling agent and/or a base.
28. The method according to embodiment 27, wherein the base is selected from the group consisting of N,N-Diisopropylethylamine (DIPEA), N,N-Diisopropylethylamine (Pr2NEt), triethylamine (TEA), 4-methylmorpholine (NMM), imidazole, pyridine, and collidine.
29. The method according to embodiment 27 or 28, wherein the coupling agent is selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethylamino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methyl-morpholinium chloride (DMTMM).
30. The method according to any of embodiments 27-29, wherein step a') is performed using a base, typically DIPEA, step d') is performed using a coupling agent and a base, typically TBTU and DIPEA, and step f) is performed using a coupling agent and a base, typically PyBOP and DIPEA.
31. The method according to any of embodiments 20-30, wherein the deprotecting agent that is used in step b') and/or e') is selected from the group consisting of hydrazine, piperidine, morpholine, 1,8-Diazabicyclo [5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine.
32. The method according to any of embodiments 20-31, wherein step c') is performed using a reductive agent, preferably selected from $NaBH_4$ and $NaBH_3CN$.
33. The method according to any of embodiments 20-32, wherein step g') is performed using trifluoroacetic acid (TFA) or a trifluoroacetic acid (TFA)/water/triisopropylsilane mixture.

The present disclosure further relates to the any one of the compounds as defined herein by the formulas from (II) to (XII) or from (II') to (XII'), or their use as intermediate in the method for synthesizing a compound of formula (I), or a pharmaceutically acceptable salt thereof. For example, in one embodiment, the present disclosure relates to the compound as defined herein by formula (II) or a pharmaceutically acceptable salt thereof. In another embodiment, the present disclosure relates to the use of the compound as defined herein by formula (II), or a pharmaceutically acceptable salt thereof, as intermediate in the method for synthesizing a compound of formula (I), or a pharmaceutically acceptable salt thereof. In the same way, further embodiments of the present disclosure as defined with respect to compounds as defined by the formula (III), (IV), (V), (VI), (VII), (VIII), (IX), (X), (XI), (XII), (II'), (III'), (IV'), (V'), (VI'), (VII'), (VIII'), (IX'), (X'), (XI') and (XII'). In another embodiment, the present disclosure relates to the use of two or more of the compounds as defined herein by any one of the formulas from (II) to (XII) or from (II') to (XII'), or a pharmaceutically acceptable salts thereof, as intermediates in the method for synthesizing a compound of formula (I), or a pharmaceutically acceptable salt thereof.

EXAMPLES

All chemicals and solvents were obtained from commercial suppliers and used without purification Fmoc-L-Lys (ivDde)-Wang PS-Resin and Fmoc-L-Glu(otbu)-Wang PS-Resin were purchased from Rapp Polymere, DE. 1,1'-Carbonyldiimidazole was purchased from SAF, DE. H-Lys (Fmoc)-OtBu·HCl, was purchased from CHI Scientific, Inc., USA. 5-Br-Benzaldehde was purchased from SAF, DE. FMOC-Aminohexanoic acid, was purchased from Iris Biotech, DE. H-Glu(OtBu)-OtBu×HCl was purchased from Bachem, CH., DOTA(tBu)3 was purchased from Macrocyclics, US.

NMR experiments were performed on a Bruker Avance Neo 500 MHZ.

Synthesis of PSMA-R2 (TFA salt); 10-(4-bromobenzyl)-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid, Trifluoroacetate Salt The synthesis of PSMA-R2 is performed by solid phase peptide synthesis technique (SPPS) using a semi-automatic batch synthesizer, SAP Multisyntech, DE., via 2 different synthesis routes.

Example 1
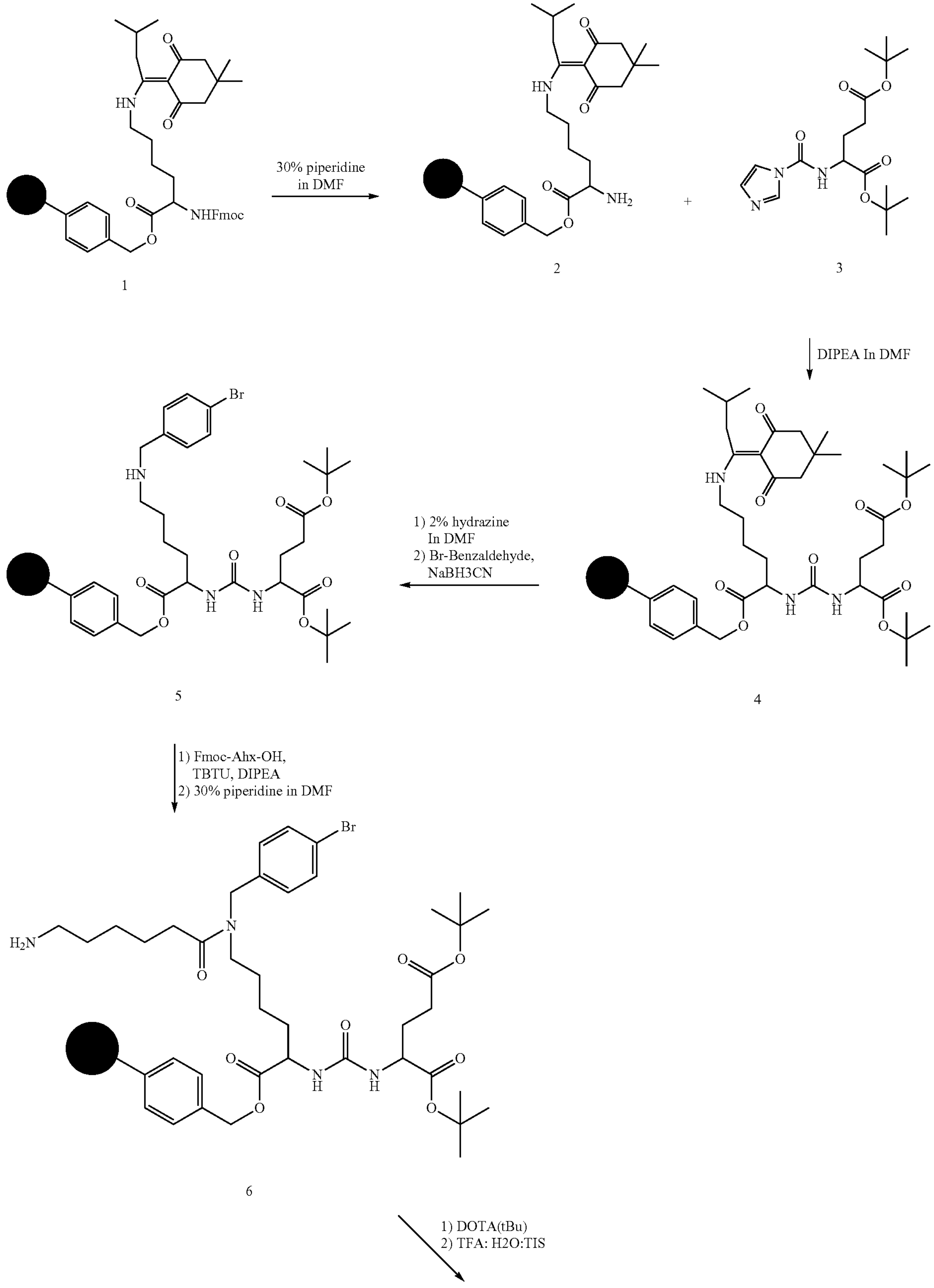

-continued

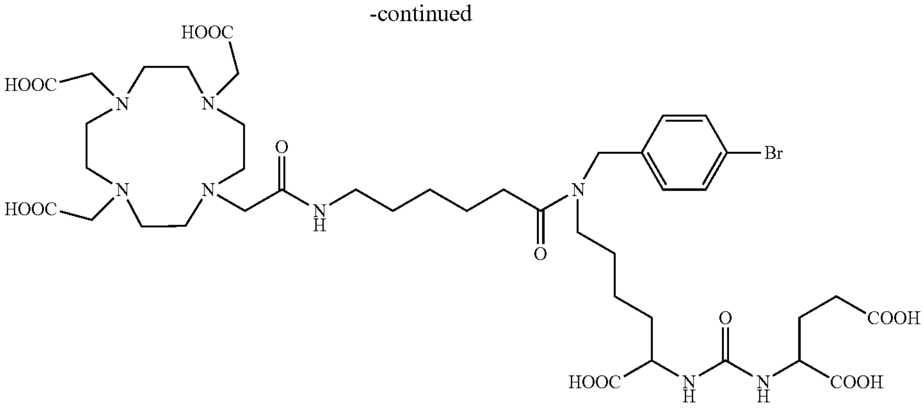

7

Synthesis of di-tert-butyl N-(1H-imidazole-1-carbonyl)glutamate Building Block [3]

1,1'-Carbonyldiimidazole (CDI) (370 mg; 1.1 eq.) is transferred into a 500 ml round flask and dissolved in dichloromethane (DCM) (100 ml). The solution is chilled to 0° C. and DIPEA (5 eq.) is added under stirring. H-Glu (OtBu)-OtBu×HCl (612 mg; 1 eq.) is dissolved in DCM (100 ml), cooled to 0° C. and added slowly to the stirred imidazole solution. The ice bath is removed and the reaction mixture is stirred at room temperature for 2-3 h. The progress of the reaction is monitored by in-process control (RP-HPLC; Nucleosil-100 RP-C18, 150×4 mm, 5 μm, gradient 10 min to 90 min in 15 min. Eluent H20/ACN 0.1% TFA).

After full conversion has been checked, the solution is reduced on a rotary evaporator. The residue is dissolved again in DCM, washed with 1 M $NaHCO_3$ and water. The organic layer is first concentrated in vacuo on a rotary evaporator and then dried on a freeze-dryer. Purity and identity of the building block are checked by RP-HPLC Nucleosil-100 RP-C18, 150×4 mm, 5 μm, gradient 10 min to 90 min in 30 min. Eluent A: H20 B:ACN (0.1% TFA) (14.8 min. with 98% purity @215 nm) and Maldi TOF-MS found [M+H]+354.3±1.0) Matrix DHB. The obtained solid was used directly for the SPPS synthesis.

Assembly of PSMA-R2 by SPPS-Approach

Synthesis of Compound [2]

1 g of Fmoc-L-Lys(ivDde)-Wang PS-Resin (0.69 mmol/g) [1] is transferred into the SPPS reaction vessel and after swelling of the resin with 10 ml DMF the FMOC group is cleaved from the resin by use of 30% Piperidine in DMF 3×10 ml. After removal of the cleavage mixture by filtration, the resin is washed 3 times with DMF and i-propanol for complete removal of the piperidine solution. FMOC removal is checked by a Ninhydrin assay as in-process control. (Lit. Weng C. Chan, Peter D. White *Fmoc Solid Phase Peptide Synthesis*. A Practical Approach. Oxford University Press, Oxford/New York 2000).

Note: If not otherwise mentioned, all coupling and FMOC-deprotection steps are checked by Ninhydrin assay.

Synthesis of Compound [4] Glu(otbu)-otBu-ureido-Lys-PS-resin

The freshly prepared building block, Di-tert-butyl N-(1H-imidazole-1-carbonyl)-glutamate (733 mg, 3 eq.) [3] is dissolved in 10 ml DMF, mixed with DIPEA (3.5 eq.) and added to the resin. The slurry is stirred for 1.5 h at RT. Excess reagents are removed by filtration followed by multiple washing steps with DMF and isopropanol (10 ml each 3 times). Completeness of the ureido-formation is checked again by Ninhydrin-assay.

Synthesis of Compound [5] Glu(otbu)-otBu-ureido-Lys(4Br-Bzl)-PS-resin

The iv-Dde protecting group at the L-lysine side chain is removed by treating the resin with 2% hydrazine monohydrate in DMF (3×10 ml) for 15 min. each time followed by filtration and multiple DMF and isopropanol washing steps (10 ml each).

3-Bromo-benzaldehyde (140 mg, 1.1 eq.) is dissolved in 5 ml MeOH, NaBH3CN (30 mg, 0.7 eq.) is dissolved in 5 ml MeOH and both solutions are directly transferred to the resin vessel and stirred for 18 h overnight.

The N-alkylation is monitored by Isatin test (Wellings, D. A.; Atherton, E. "Methods in Enzymology Volume 289: Solid-Phase Peptide Synthesis" Ed. Fields, G. B. Academic Press, San Diego, 1997). Additionally, a test cleavage of a small resin sample is performed and almost full conversion to the benzyl derivative is confirmed by HPLC and MS analysis.

Synthesis of compound [6] Fmoc-Ahx-OH (730 mg, 3 eq.) is activated by in situ active ester formation using (TBTU) 3 eq. and DIPEA 3 eq. in 5 ml DMF and added to the resin, stirred for 1 hour at RT. Due to incomplete conversion, as shown by in-process control, a double coupling is performed using the identical procedure followed by FMOC-cleavage, resulting the resin bound Glu(otbu)-otBu-ureido-Lys(N-4-Br-Bzl-,N-Ahx)-PS-resin.

Synthesis of Compound [7]

(DOTA(tBu)3) (987 mg, 2.5 eq.) is coupled to the resin attached peptide by use of (1H-benzotriazol-1-yloxy)tripyrrolidino-phosphonium hexafluorophosphate (PyBOP) (2.5 eq.), DIPEA (5 eq.) dissolved in 10 ml DMF. The DOTA attachment is confirmed by Ninhydrin assay and by a test cleavage analyzed by HPLC and Maldi-TOF MS. Finally, the resin is transferred to a sintered glass funnel and the resin bound peptide is washed extensively with DMF, methanol and diethyl ether and dried.

The peptide is cleaved from the solid support by incubation with 15 ml cleavage cocktail, TFA:$H_2O$:TIS (94:3:3) for 3.5 hours at RT. The resin is removed by filtration, washed carefully with small portion of TFA and the pooled cleavage solution is chilled and the product is precipitated by dripping the peptide solution into ice-cooled diethyl ether. The product is isolated by centrifugation; the precipitate is washed with diethyl ether, dried in vacuo and finally dissolved in a mixture of 10% acetonitrile in water and freeze-dried to obtain 488 mg crude product as a lyophilisate [7]. The purity (23%) of the crude product was determined by HPLC and Maldi-TOF.

The purification of the product is done using preparative RP-HPLC method (Luna, RP-18(3), 200×25 mm, 10 μm) with water/acetonitrile (0.1% TFA) as eluent, choosing a gradient systems (25% acetonitrile to 45% acetonitrile within 30 min, flowrate 21 ml, UV @225 nm). All fractions that meet specifications for RP-HPLC-purity (≥98.0% were pooled and freeze-dried. All other fraction were reprocessed until specifications are met. Overall yield was 102 mg lyophilisate; 15% theor. based on resin loading.

Analysis of the synthesized molecules was performed using Nucleosil-100 RP-18, 150×4 mm, 5 μm; 1 mL/min @UV 215 nm; solvent A: H20 (0.1% TFA) B: CH3CN (0.1% TFA) with a linear gradient (10% B to 90% B in 30 min). Product elutes at 10.3 min.

Mass spectrometry MALDI-MS (Kratos Axima) Calcd. for C41H63BrN8O15 986.36 amu. Found [M+H+]: 987.3 m/z.

Elemental analysis using the nitrogen value only (CHN theory: C, 49.85; H, 6.43; N, 11.34; (8.69% found) a net peptide content of 76.6% (w/w) was determined.

NMR:

Proposed structure was also confirmed by 2D-DQ-COSY, 2D-TOCSY, 2D-ROESY and 13C-HSQC NMR experiments on a Bruker Avance Neo 500 MHZ.

FIG. 1 Represents H-NMR Overlay with Another Batch Produced by Conventional Method Proofs.

1D 1H spectrum with Watergate H2=suppression, serving for reference and as fingerprint

Example 2

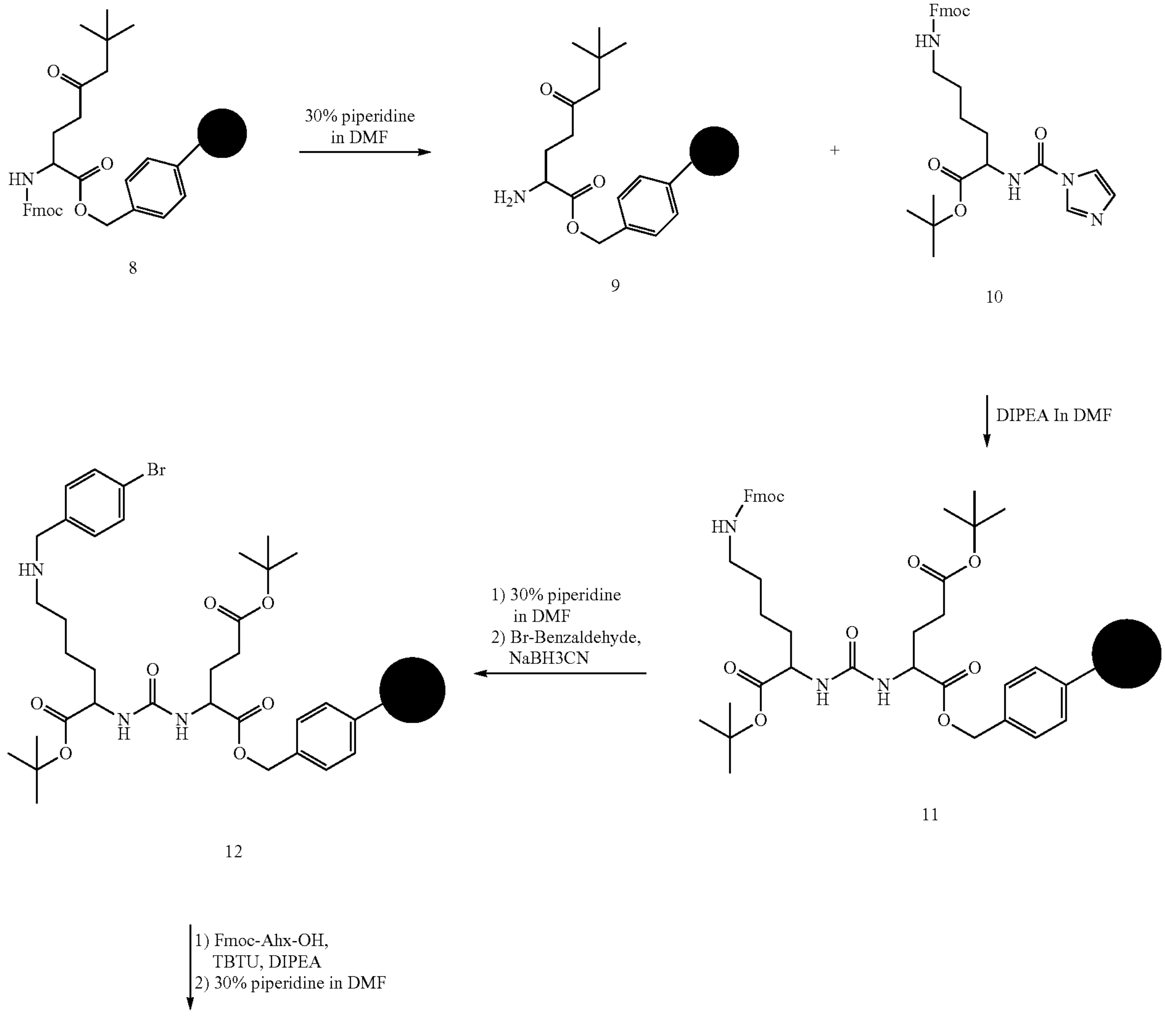

8

9

10

11

12

-continued

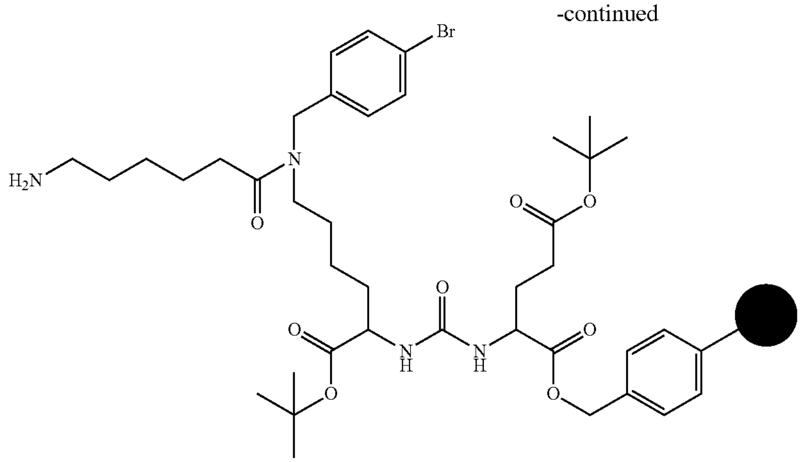

13

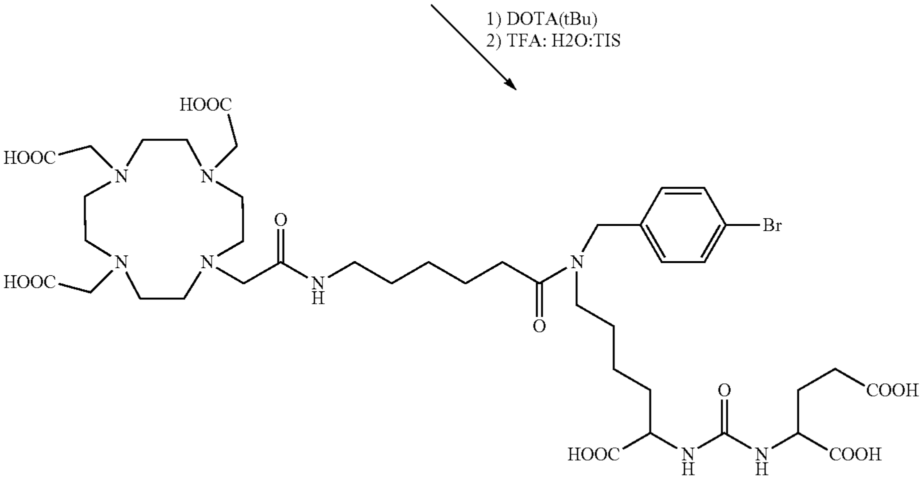

7

Synthesis of tert-butyl N6-(((9H-fluoren-9-yl) methoxy)carbonyl)-N2-(1H-imidazole-1-carbonyl) lysinate (Building Block [10]

1,1'-Carbonyldiimidazole (CDI) (348 mg; 1.1 eq.) is transferred into a 250 ml round flask and dissolved in dichloromethane (30 ml). The solution is chilled to 0° C. and DIPEA (5 eq.) is added under stirring.

H-Lys(FMOC)-OtBu×HCl (900 mg; 1 eq.) is dissolved in DCM (30 ml), cooled to 0° C. and added slowly to the stirred imidazole solution. The ice bath is removed and the reaction mixture is stirred at room temperature for 3 hours. The progress of the reaction is monitored by in-process control (RP-HPLC; Nucleosil-100 RP-C18, 150×4 mm, 5 μm, gradient 10 min to 90 min in 15 min. Eluent H20/ACN 0.1% TFA). After conversion is completed, the solution is reduced on a rotary evaporator. The residue is dissolved in DCM, washed with 1 M $NaHCO_3$ and water. The organic layer is first concentrated in vacuo on a rotary evaporator and then dried on a freeze-dryer. The white solid is then used directly for the assembly of the ureido compound. Purity and identity of the building block are checked by RP-HPLC and MS. Nucleosil-100 RP-C18, 150×4 mm, 5 μm, gradient 10 min to 90 min in 30 min. Eluent: H20/ACN 0.1% TFA; Maldi TOF-MS ([M+H]+518.6±1.0) Matrix DHB.

Assembly of PSMA-R2 by FMOC-SPPS-Strategy

Synthesis of Compound [9]

1.0 g of Fmoc-L-Glu(otBu)-Wang resin (0.65 mmol/g) [8] is transferred into the reaction vessel and swelled with 10 ml DMF, the FMOC group then is cleaved by use of 30% Piperidine in DMF (3×15 ml).

The FMOC cleavage solution is removed by filtration and washed excessively by DMF/i-propanol washing steps.

General note: As in-process control if not otherwise mentioned, for each removal of the FMOC protecting group and each elongation step a Ninhydrin assay is used. (Lit. Weng C. Chan, Peter D. White; Fmoc Solid Phase Peptide Synthesis. A Practical Approach. Oxford University Press, Oxford/New York 2000).

Synthesis of Compound 11

The freshly prepared N6-(((9H-fluoren-9-yl)methoxy) carbonyl)-N2-(1H-imidazole-1-carbonyl) lysinate 1.01 g (3 eq.) [10] is dissolved in 10 ml DMF, mixed with DIPEA (3.5 eq.) and added to the resin. The slurry is stirred for 2 h at RT.

Excess coupling reagents are removed by filtration, followed by multiple washing steps with DMF and isopropanol (15 ml each time).

Synthesis of Compound [12] Lys-otbu-ureido-Glu(otbu)-PS-resin

FMOC group of the L-Lys side is cleaved using 30% piperidine in DMF followed by consecutive washing steps DMF/i-propanol/DMF (3×10 ml each).

3-Bromo-benzaldehyde (132 mg, 1.1 eq.) is dissolved in 5 ml MeOH, NaBH3CN (35 mg, 0.85 eq.) is dissolved in 5 ml MeOH and both solutions are directly transferred to the resin vessel and stirred overnight.

The N-alkylation is monitored by Isatin test (Wellings, D. A.; Atherton, E. "Methods in Enzymology Volume 289: Solid-Phase Peptide Synthesis" Ed. Fields, G. B. Academic Press, San Diego, 1997).

Synthesis of Compound [13]

Fmoc-Ahx-OH (690 mg, 3 eq.) is activated by in situ active ester formation using (TBTU) 3 eq. and DIPEA 3 eq. in 5 ml DMF and added to the resin, stirred for 1 hour at RT. Due to incomplete conversion, as shown by in-process control, a double coupling is required using the identical procedure followed by FMOC-cleavage, resulting the resin bound Lys(N-4-Br-Bzl-,N-Ahx)otBu-ureido-Glu(otbu)PS-resin [13].

Synthesis of compound [7] (DOTA(tBu)3) (930 mg, 2.5 eq.) is coupled to the resin attached peptide by use of (1H-benzotriazol-1-yloxy)tripyrrolidino-phosphonium hexafluorophosphate (PyBOP) (2.5 eq.), DIPEA (5 eq.) dissolved in 10 ml DMF. The DOTA attachment is confirmed by Ninhydrin assay and by a test cleavage analyzed by HPLC and Maldi-TOF MS. Finally, the peptide resin is transferred to a sintered glass funnel and the resin bound peptide is washed extensively with DMF, methanol and diethyl ether and dried.

The peptide is cleaved from the solid support by incubation with 15 ml cleavage cocktail, TFA:$H_2O$:TIS (94:3:3) for 3 hours at RT. The resin is removed by filtration, washed carefully with small portion of TFA and the pooled cleavage solution is chilled and the product is precipitated by dripping the peptide solution into stirred ice-cooled diethyl ether. The product is isolated by centrifugation; the precipitate is washed with diethyl ether, dried in vacuo and finally dissolved in a mixture of 10% acetonitrile in water and freeze-dried to obtain 435 mg crude product as a lyophilisate [7]. The purity (23%) of the crude product was determined by HPLC and Maldi-TOF.

The purification and isolation of the product is done according to example 1.

Overall yield including SPPS and purification was 14% (89 mg) based on resin loading.

The purity was checked by HPLC and Maldi-TOF MS. HPLC spiking experiments confirms identity with the product derived from example 1.

The invention claimed is:

1. A method for synthesizing a compound of formula (I), or a pharmaceutically acceptable salt thereof, using solid phase synthesis:

(I)

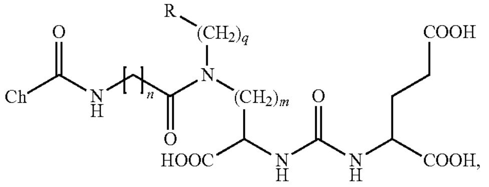

wherein m is an integer selected from the group consisting of 1, 2, 3, 4, and 5;

q is an integer selected from the group consisting of 1, 2, 3, 4, 5, and 6;

n is an integer selected from the group consisting of 1, 2, 3, 4, 5, and 6;

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene;

Y is a halogen; and

Ch is a chelating agent, wherein said method comprises all of the following steps:

a) contacting a supported compound of formula (II)

(II)

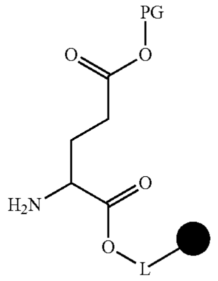

with a compound of formula (III)

(III)

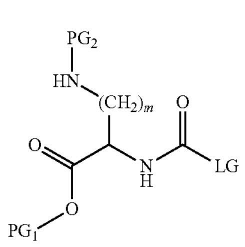

to provide a supported compound of formula (IV)

(IV)

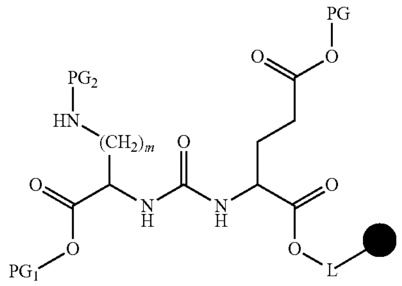

b) contacting the supported compound of formula (IV) with a deprotecting agent to provide a supported compound of formula (V)

(V)

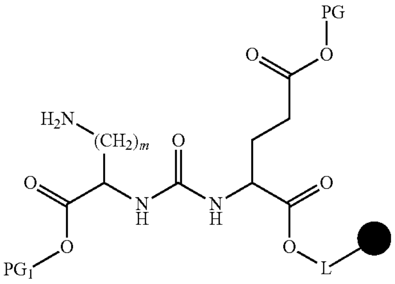

c) contacting the supported compound of formula (V) with a compound of formula (VI)

(VI)

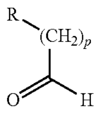

to provide a supported compound of formula (VII)

(VII)

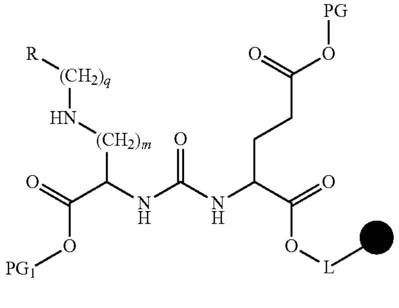

d) contacting the supported compound of formula (VII) with a compound of formula (VIII)

(VIII)

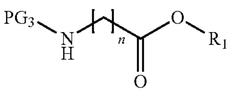

to provide a supported compound of formula (IX)

(IX)

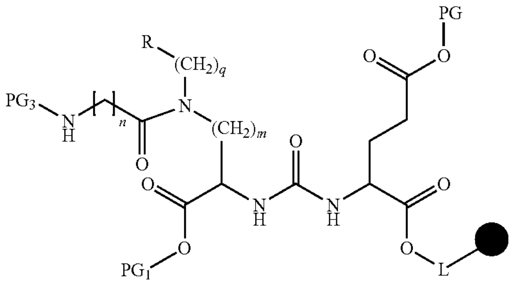

e) contacting the supported compound of formula (IX) with a deprotecting agent to provide a supported compound of formula (X)

(X)

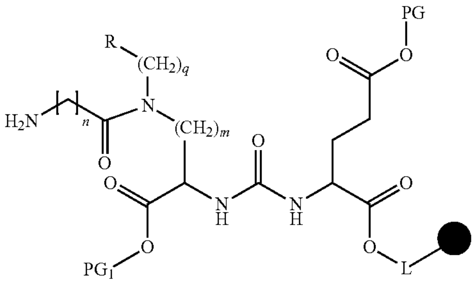

f) contacting the supported compound of formula (X) with a compound of formula (XI)

(XI)

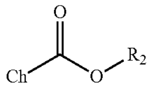

to provide a supported compound of formula (XII)

(XII)

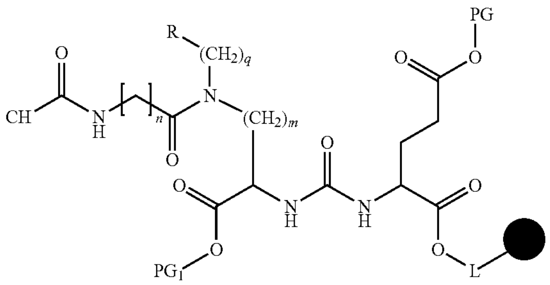

g) contacting the supported compound of formula (XII) with a cleavage reagent, and optionally with a deprotecting agent, to provide the compound of formula (I)

wherein

PG, and PG1 are each independently a carboxyl protecting group a carboxyl protecting group;

L is a linker;

PG2 and PG3 are each independently an amino protecting group;

R1 and R2 are each independently H, an activating ester group;

LG is a leaving group selected from the group consisting of imidazole, halogens and activating ester groups, and p=q−1.

2. The method according to claim 1, wherein R is selected from

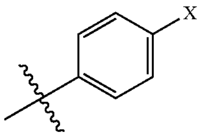

and

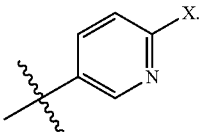

3. The method according to claim 1, wherein Ch is selected from the group consisting of:

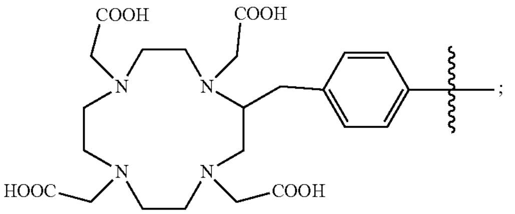

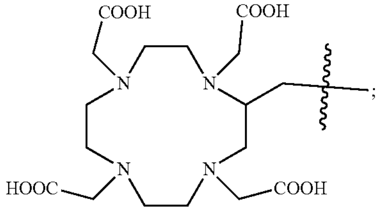

-continued

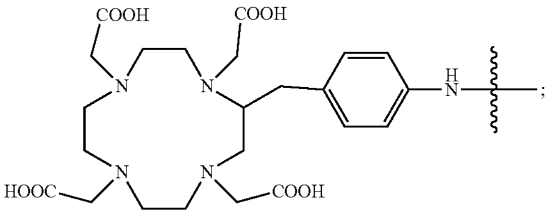

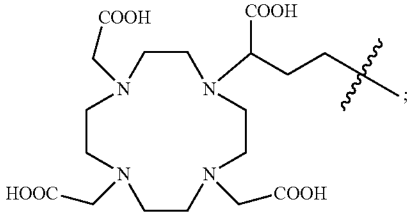

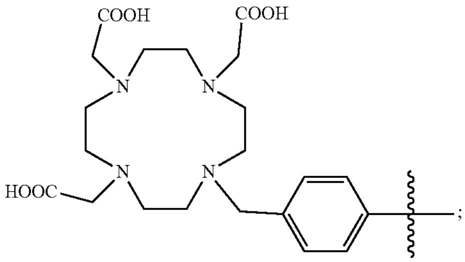

and

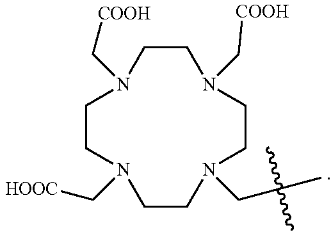

4. The method according to claim 1, wherein said compound of formula (I) is a compound of formula (XIII)

(XIII)

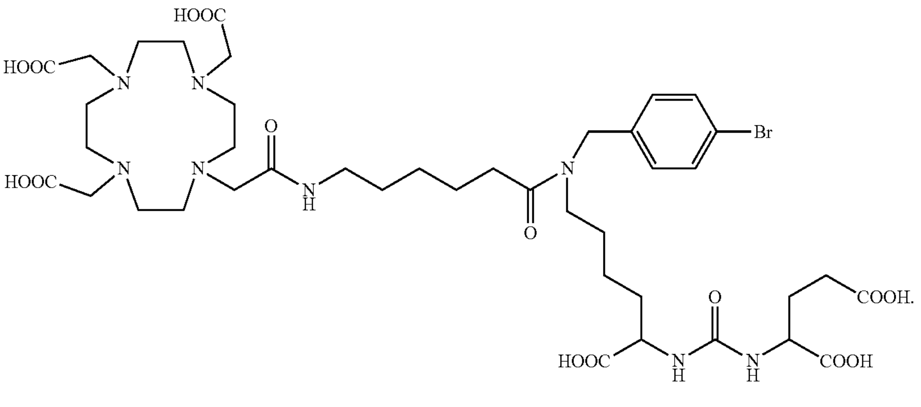

5. The method according to claim 1, wherein said compound of formula (I) is a compound of formula (XIV)

(XIV)

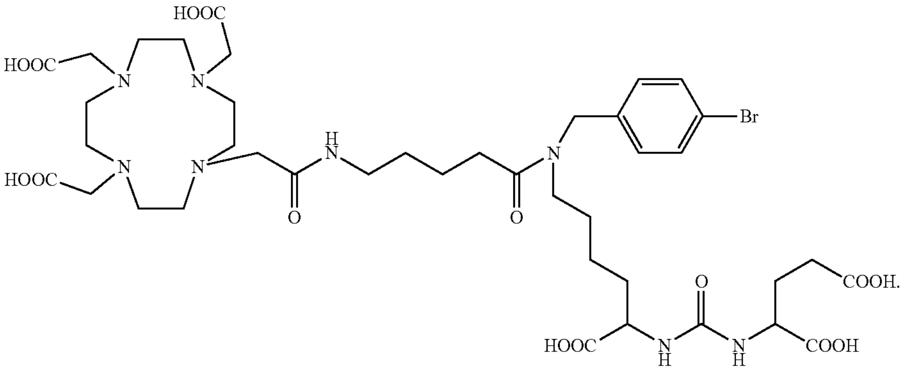

6. The method according to claim 1, wherein PG, and PG1 are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

7. The method according to claim 1, wherein PG2, and PG3, are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene) ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt).

8. The method according to claim 1, wherein at least one of the step a), d) or f) is performed using a coupling agent and/or a base.

9. A method for synthesizing a compound of formula (I), or a pharmaceutically acceptable salt thereof, using solid phase synthesis:

(I)

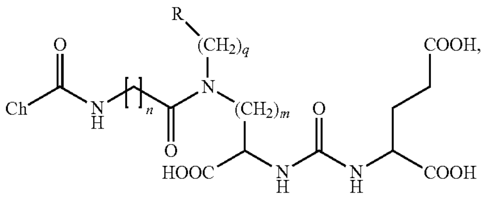

wherein m is an integer selected from the group consisting of 1, 2, 3, 4, and 5;

q is an integer selected from the group consisting of 1, 2, 3, 4, 5, and 6;

n is an integer selected from the group consisting of 1, 2, 3, 4, 5, and 6;

R is selected from the group consisting of $C_6$-$C_{10}$ aryl and heteroaryl containing 5 to 10 ring atoms, said aryl and heteroaryl being substituted 1 or more times with X;

X is —V—Y;

V is a bond or a $C_1$-$C_6$ alkylene;

Y is a halogen; and

Ch is a chelating agent, wherein said method comprises all of the following steps:

a') contacting a supported compound of formula (II')

(II')

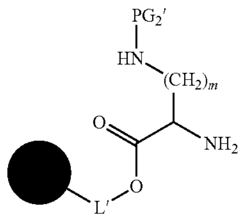

with a compound of formula (III')

(III')

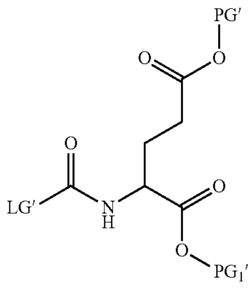

to provide a supported compound of formula (IV')

(IV')

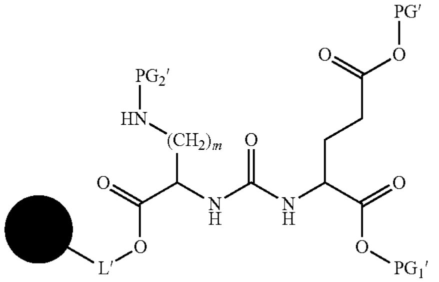

b') contacting the supported compound of formula (IV') with a deprotecting agent to provide a supported compound of formula (V')

(V')

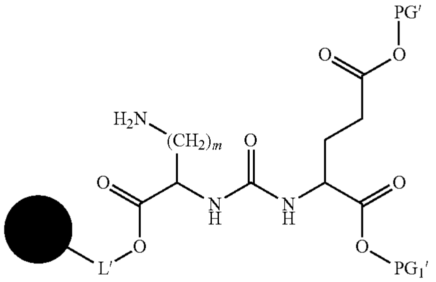

c') contacting the supported compound of formula (V') with a compound of formula (VI')

(VI')

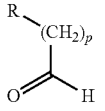

to provide a supported compound of formula (VII')

(VII')

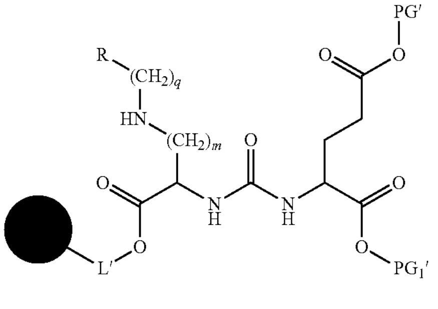

d') contacting the supported compound of formula (VII') with a compound of formula (VIII')

(VIII')

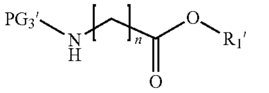

to provide a supported compound of formula (IX')

(IX')

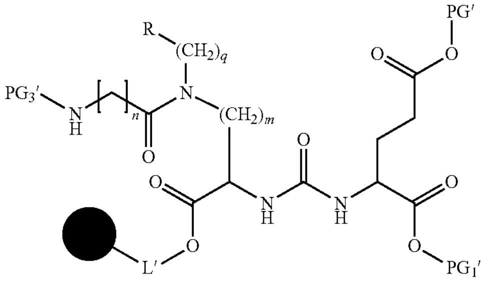

e') contacting the supported compound of formula (IX') with a deprotecting agent to provide a resin-based compound of formula (X')

(X')

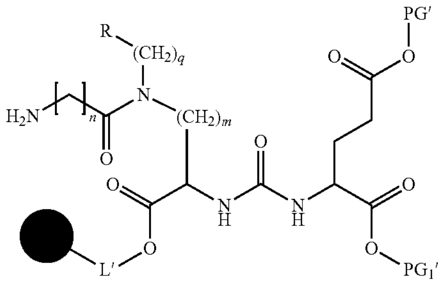

f) contacting the supported compound of formula (X') with a compound of formula (XI')

(XI')

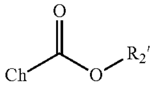

to provide a supported compound of formula (XII')

(XII')

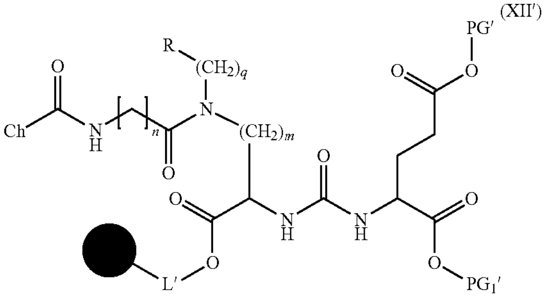

g') contacting the supported compound of formula (XII') with a cleavage reagent, and optionally with a deprotecting agent, to provide the compound of formula (I), wherein PG', and PG1' are each independently a carboxyl protecting group a carboxyl protecting group;

L' is a linker;

PG2' and PG3' are each independently an amino protecting group;

R1' and R2' are each independently H, an activating ester group;

LG' is a leaving group selected from the group consisting of imidazole, halogens and activating ester groups;

p=q−1.

10. The method according to claim 9, wherein PG', and PG1' are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

11. The method according to claim 9, wherein PG2', and PG3', are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene) ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt).

12. The method according to claim 9, wherein at least one of the step a'), d') or f') is performed using a coupling agent and/or a base.

13. The method according to claim 9, wherein R is selected from

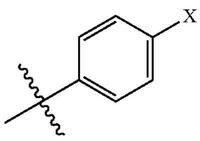

and

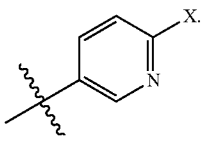

14. The method according to claim 9, wherein Ch is selected from the group consisting of:

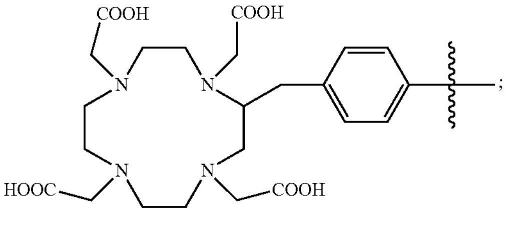

;

-continued

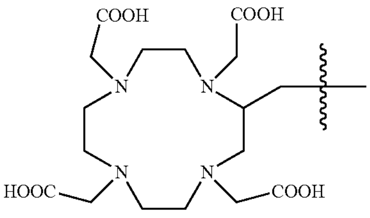

;

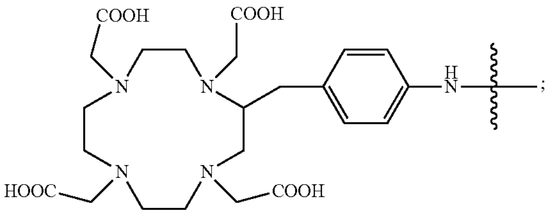

;

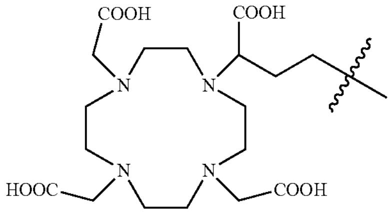

;

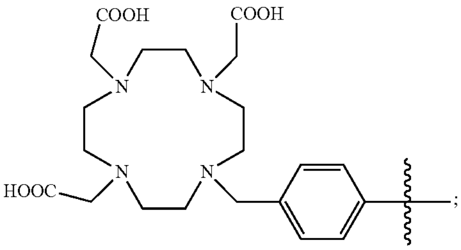

; and

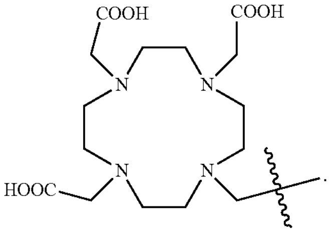

.

15. The method according to claim 9, wherein said compound of formula (I) is a compound of formula (XIII)

(XIII)
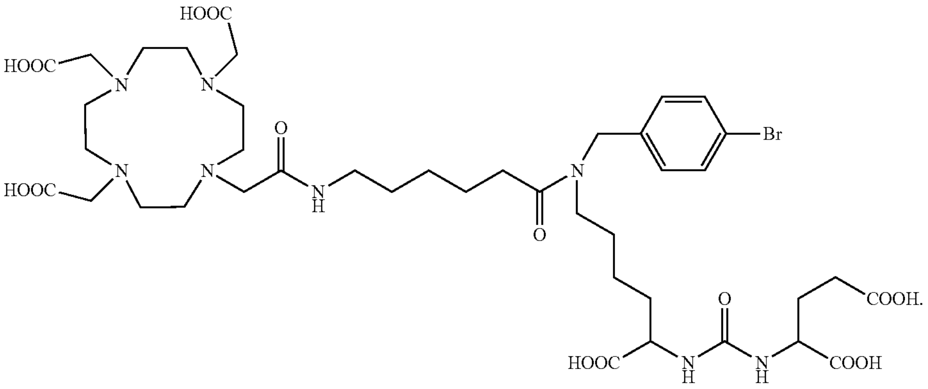
16. The method according to claim 9, wherein said compound of formula (I) is a compound of formula (XIV)
(XIV)
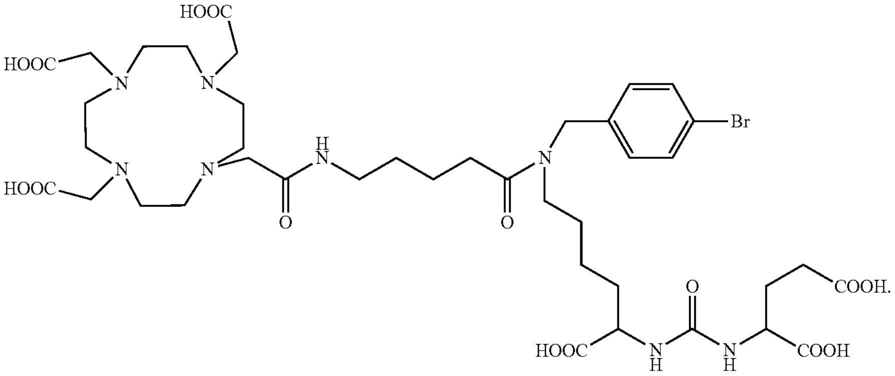
* * * * *